(12) United States Patent
Arnold et al.

(10) Patent No.: US 8,017,074 B2
(45) Date of Patent: Sep. 13, 2011

(54) STERILIZATION SYSTEM AND DEVICE

(75) Inventors: Ernst V. Arnold, Hagerstown, MD (US); Blaine G. Doletski, Elkridge, MD (US); Thomas M. Dunn, Palmyra, PA (US); Robert E. Raulli, Manassas, VA (US); Edward P. Mueller, Annapolis, MD (US); Karen R. Benedek, Winchester, MA (US); Marie-Louise Murville, Washington, DC (US)

(73) Assignee: Noxilizer, Inc., Washington, DC (US)

( * ) Notice: Subject to any disclaimer, the term of this patent is extended or adjusted under 35 U.S.C. 154(b) by 895 days.

(21) Appl. No.: 11/477,513

(22) Filed: Jun. 30, 2006

(65) Prior Publication Data
US 2007/0014686 A1 Jan. 18, 2007

Related U.S. Application Data

(63) Continuation-in-part of application No. PCT/US2005/000173, filed on Jan. 6, 2005.

(60) Provisional application No. 60/564,589, filed on Jul. 23, 2004, provisional application No. 60/575,421, filed on Jun. 1, 2004, provisional application No. 60/534,395, filed on Jan. 7, 2004.

(51) Int. Cl.
*A61L 2/20* (2006.01)
*A61L 2/00* (2006.01)
*A61L 2/18* (2006.01)
*A61L 9/00* (2006.01)

(52) U.S. Cl. ............. 422/33; 422/28; 422/292; 422/295
(58) Field of Classification Search .................. 422/295, 422/28, 33, 292
See application file for complete search history.

(56) References Cited

U.S. PATENT DOCUMENTS

| | | | | |
|---|---|---|---|---|
| 4,756,882 A | * | 7/1988 | Jacobs et al. | 422/23 |
| 4,770,851 A | * | 9/1988 | Joslyn | 422/26 |
| 5,122,344 A | * | 6/1992 | Schmoegner | 422/111 |
| 5,236,609 A | | 8/1993 | Smith | |
| 5,578,280 A | * | 11/1996 | Kazi et al. | 422/186.07 |
| 5,633,424 A | | 5/1997 | Graves | |
| 5,674,450 A | * | 10/1997 | Lin et al. | 422/29 |

(Continued)

FOREIGN PATENT DOCUMENTS

CA 2208754 C 12/2007

(Continued)

OTHER PUBLICATIONS

Kelly-Wintenberg, et al. Room temperature sterilization of surfaces and fabrics with a One Atmosphere Uniform Glow Discharge Plasma, (1998), Journal of Industrial Microbiology & Biotechnology, 20, pp. 69-74.*

(Continued)

*Primary Examiner* — Sean E Conley
*Assistant Examiner* — Regina Yoo
(74) *Attorney, Agent, or Firm* — Pillsbury Winthrop Shaw Pittman LLP

(57) ABSTRACT

A system, device and method for sterilizing or decontaminating an object that by exposing the object to a sterilant gas comprised of one or more oxides of nitrogen, such as NO, $NO_2$, $NO_3$, $N_2O_3$, $N_2O_4$, $N_2O_5$, $N_2O$ and mixtures thereof. The source of the sterilant gas can be generated from a sterilant gas-generating composition or provided by a source of the sterilant gas.

40 Claims, 3 Drawing Sheets

U.S. PATENT DOCUMENTS

| | | | |
|---|---|---|---|
| 5,785,934 A | 7/1998 | Jacobs et al. | |
| 5,814,666 A | 9/1998 | Green | |
| 5,830,409 A * | 11/1998 | Childers et al. | 422/30 |
| 5,939,033 A | 8/1999 | Kendall et al. | |
| 5,965,264 A * | 10/1999 | Barenberg et al. | 428/402 |
| 6,046,243 A * | 4/2000 | Wellinghoff et al. | 514/772.3 |
| 6,103,769 A | 8/2000 | Kelm | |
| 6,119,480 A | 9/2000 | Germain | |
| 6,232,336 B1 | 5/2001 | Hrabie et al. | |
| 6,524,624 B1 | 2/2003 | Morelli et al. | |
| 6,673,338 B1 | 1/2004 | Arnold et al. | |
| 7,045,096 B2 | 5/2006 | D'Ottone | |
| 7,288,664 B2 | 10/2007 | Kleiner | |
| 2001/0000039 A1 | 3/2001 | Toone | |
| 2001/0041184 A1 | 11/2001 | Fitzhugh | |
| 2001/0043890 A1* | 11/2001 | Son | 422/174 |
| 2002/0009604 A1 | 1/2002 | Zamora | |
| 2002/0051730 A1* | 5/2002 | Bodnar et al. | 422/33 |
| 2002/0082566 A1 | 6/2002 | Stenzler | |
| 2002/0085950 A1* | 7/2002 | Robitaille et al. | 422/28 |
| 2002/0098979 A1 | 7/2002 | Cutler | |
| 2002/0136750 A1 | 9/2002 | Benjamin et al. | |
| 2003/0012804 A1 | 1/2003 | Cutler | |
| 2003/0021825 A1 | 1/2003 | Pathak | |
| 2003/0175408 A1* | 9/2003 | Timm et al. | 427/2.1 |
| 2003/0196966 A1 | 10/2003 | Hughes | |
| 2003/0228564 A1 | 12/2003 | Edrich | |
| 2004/0022676 A1* | 2/2004 | Hamilton et al. | 422/37 |
| 2004/0028596 A1 | 2/2004 | Kleiner | |
| 2004/0037736 A1 | 2/2004 | Perruchot et al. | |
| 2004/0087963 A1 | 5/2004 | Ossipov | |
| 2004/0121940 A1 | 6/2004 | De Groot | |
| 2004/0220265 A1 | 11/2004 | Martin | |
| 2005/0113450 A1 | 5/2005 | Thorarensen | |
| 2005/0158206 A1 | 7/2005 | Moisan | |
| 2005/0186310 A1 | 8/2005 | Paganessi | |
| 2005/0203069 A1 | 9/2005 | Arnold et al. | |
| 2005/0279713 A1 | 12/2005 | Osborn | |
| 2006/0020166 A1 | 1/2006 | Berall | |
| 2006/0068031 A1 | 3/2006 | Miller | |
| 2006/0088469 A1 | 4/2006 | Perez-Ramirez | |
| 2006/0095120 A1 | 5/2006 | Herrmann | |
| 2006/0165858 A1 | 7/2006 | Yuan | |
| 2006/0251824 A1 | 11/2006 | Boulais | |
| 2006/0275340 A1 | 12/2006 | Udipi | |
| 2007/0003589 A1 | 1/2007 | Astafieva et al. | |
| 2007/0014686 A1 | 1/2007 | Arnold et al. | |
| 2007/0087025 A1 | 4/2007 | Fitzhugh | |
| 2007/0116785 A1 | 5/2007 | Miller | |
| 2007/0196428 A1 | 8/2007 | Glauser | |
| 2007/0224239 A1 | 9/2007 | Behan | |
| 2007/0225785 A1 | 9/2007 | Park | |
| 2007/0264225 A1 | 11/2007 | Cheng | |
| 2007/0275100 A1 | 11/2007 | Miller | |
| 2007/0286882 A1 | 12/2007 | Tang | |
| 2008/0029093 A1 | 2/2008 | Stenzler | |
| 2008/0097575 A1 | 4/2008 | Cottone | |
| 2008/0175881 A1 | 7/2008 | Ippoliti | |
| 2008/0183276 A1 | 7/2008 | Melder | |
| 2008/0213403 A1 | 9/2008 | Martin | |
| 2008/0220046 A1 | 9/2008 | Cheng | |
| 2008/0220048 A1 | 9/2008 | Chen | |
| 2008/0233212 A9 | 9/2008 | Miller | |
| 2008/0268524 A1 | 10/2008 | Cachon | |
| 2008/0286321 A1 | 11/2008 | Reneker | |
| 2008/0314289 A1 | 12/2008 | Pham | |
| 2008/0317626 A1 | 12/2008 | Arnold | |
| 2008/0317813 A1 | 12/2008 | Craig | |
| 2008/0317939 A1 | 12/2008 | Dehnad | |
| 2009/0022769 A1 | 1/2009 | Chen | |
| 2009/0035350 A1 | 2/2009 | Stankus | |
| 2009/0041845 A1 | 2/2009 | Kleiner | |

FOREIGN PATENT DOCUMENTS

| | | |
|---|---|---|
| CA | 2582887AA | 12/2007 |
| CN | 1505930 A | 6/2004 |
| EP | 0410118 B1 | 4/1994 |
| EP | 0674845 A1 | 10/1995 |
| EP | 0818212 A3 | 7/1998 |
| EP | 1704877 A1 | 9/2006 |
| EP | 1722223 A1 | 11/2006 |
| EP | 1370298 B1 | 10/2008 |
| GB | 983073 A | 2/1965 |
| GB | 2384185 A | 11/2003 |
| JP | 63126598 A2 | 5/1988 |
| JP | 2-134322 A2 | 5/1990 |
| JP | 2-208204 A2 | 8/1990 |
| JP | 3-77698 A2 | 4/1991 |
| JP | 3-282101 A2 | 12/1991 |
| JP | 4-66510 A2 | 3/1992 |
| JP | 4-118099 A2 | 4/1992 |
| JP | 2001198419 A2 | 7/2001 |
| KR | 2000-0030368 A | 6/2000 |
| KR | 2003-0067338 A | 8/2003 |
| KR | 10-2004-038041 A | 5/2004 |
| RU | 2260959 C2 | 9/2005 |
| WO | WO9116083 A1 | 10/1991 |
| WO | WO 96/09210 | 3/1996 |
| WO | WO 96/31217 | 10/1996 |
| WO | WO9631217 A1 | 10/1996 |
| WO | WO9805689 A1 | 2/1998 |
| WO | WO9956892 A1 | 11/1999 |
| WO | WO 99/67210 | 12/1999 |
| WO | WO9967210 A1 | 12/1999 |
| WO | WO0186289 A1 | 11/2001 |
| WO | WO0243786 A2 | 6/2002 |
| WO | WO03017996 A1 | 3/2003 |
| WO | WO03026717 A1 | 4/2003 |
| WO | WO03/047777 | 6/2003 |
| WO | WO03/051407 | 6/2003 |
| WO | WO 03/063914 A2 | 8/2003 |
| WO | WO03066109 A1 | 8/2003 |
| WO | WO 03/080132 A1 | 10/2003 |
| WO | WO2004011039 A2 | 2/2004 |
| WO | WO2004018368 A1 | 3/2004 |
| WO | WO2004067448 A1 | 8/2004 |
| WO | WO2005029036 A2 | 3/2005 |
| WO | WO 2005/044315 A2 | 5/2005 |
| WO | WO 2005/067986 | 7/2005 |
| WO | WO2005067986 A1 | 7/2005 |
| WO | WO2005082174 A1 | 9/2005 |
| WO | WO2005105065 A2 | 11/2005 |
| WO | WO2006053004 A2 | 5/2006 |
| WO | WO2006100156 A2 | 9/2006 |
| WO | WO2006128121 A2 | 11/2006 |
| WO | WO2007005910 A2 | 1/2007 |
| WO | WO2007008618 A2 | 1/2007 |
| WO | WO2007015739 A2 | 2/2007 |
| WO | WO2007036775 A1 | 4/2007 |
| WO | WO2007067477 A1 | 6/2007 |
| WO | WO2007092043 A2 | 8/2007 |
| WO | WO2007146231 A2 | 12/2007 |
| WO | WO2008005313 A2 | 1/2008 |
| WO | WO2008018820 A1 | 2/2008 |
| WO | WO2008051881 A2 | 5/2008 |
| WO | WO2008055718 A3 | 5/2008 |
| WO | WO2008095841 A2 | 8/2008 |
| WO | WO2008112391 A2 | 9/2008 |
| WO | WO2008127889 A2 | 10/2008 |
| WO | WO2008148013 A1 | 12/2008 |
| WO | WO2009017855 A2 | 2/2009 |

OTHER PUBLICATIONS

Gadri et al. Sterilization and plasma procesing of room temperature surfaces with a one atmosphere uniform glow discharge plasma (OAUGDP), (2000), Surface and Coatings Technology, 131, pp. 528-542.*

R Ehrlich and S Miller, "Effect of NO2 on Airborne Venezuelan Equine Encephalomyelitis Virus," Applied Microbiology 23 (1972): 481-484.*

PCT search report dated Dec. 6, 2007 (in English).

Bhat, et al., "N-Nitroso-N, O-Dialkylhydroxylamines: Preparation, Structure, and Mechanism of the Hyronium Ion Catalysed Solvolytic Nitrous Oxide Extrusion Reaction," J. Chem. Soc., Perkin Trans.2, 2000 p. 1435-1446, vol. 7.

Ellies et al., "Crystallographic structure and surface morphology of sintered carbonated apatites," *J. Biomed Mater. Res.*, 1998, 22(6):541-53.
EP 05704995.9 Supplementary European Search Report Completed on Apr. 16, 2009.
Enomoto et al., "Inactivation of food microorganisms by high-pressure carbon dioxide treatment with or without explosive decompression," *Biosci. Biotech. Biochem.*, 1997, 61(7):1133-7.
Hetrick, et al., "Reducing implant-related infections: active release strategies," *Chem. Soc. Rev.*, 2006, 35(9):780-9.
Populaire, et al., "An armoured endotracheal tube obstruction in a child," *Can. J. Anaesth.*, 1989, (3 pt 1) 331-2.
Sharpless et al., "Impact of hydrogen peroxide on nitrite formation during UV disinfections," *Water Res.*, 2003, 37(19):4730-6.
Sharpless et al., "UV photolysis of nitrate: effects of natural organic matter and dissolved in organic carbone and implications for UV water disinfection," *Environ Sci. Technol.*, 2001, 35(14):2949-55.
Smith et al., "Dental implant materials. I. Some effect of preparative procedures on surface topography," *J. Biomed Mater Res.*, 1991, 9:1045-68.
Young et al., "Microwave sterilization of nitrous oxide nasal hoods contaminated with virus," *Oral Surg. Oral Med Oral Pathol.* 1985, 60(6): 58-585.
P. Dinee, "Antibacterial activity of oxidized regenerated cellulose" *Surgery, Gynecology & Obstetrics*, 1976, vol. 142, No. 4, pp. 481-486 (abstract only).
R. H. Hasek et al., "Oxidation of Cellulose," *Industrial and Engineering Chemistry*, Jan. 1949, pp. 2-8, vol. 41, No. 1.
Virginia Kneeland Frantz, "Absorbable Cotton, Paper and Gauze," *From the Department of Surgey and the Surgical Pathology Laboratory College of Physicians and Surgeons, Columbia University*, Jul. 1943, pp. 116-126, vol. 118, No. 1.
James Kulla et al., "Sterilizing Combination Products Using Using Oxides of Nitrogen" MedicalDevice_Lind.com, Mar. 2009, Web. Mar. 5, 2009, http://www.deviceling.com/grabber/php3?URL=http://www.dvicelink.com/mddi/archive.
A. A. Polyakov et al., "Bactericidic Action of Nitrogen Dioxide on the Vegetative and Sporous Forms of *Bacillus anthracis," Journal of Microbiology*, 1962, pp. 43-45, vol. 24, No. 6, Translation No. 985, Nov. 1963, pp. 1-3, U.S. Army Biological Laboratories Fort Detrick, Frederick, Maryland.
"Recent Developments in Sterilization Technology" *Medical Plastics and Biomaterials Magazine*, Sep. 1998, http://www.mddionline.com.
E. W. Rice et al., "Inactivation of Spores of *Bacillus anthracis* Stern, *Bacillus cereus*, and *Bacillus thuringiensis* subsp. *israelensis* by Chlorination," *Applied and Environmental Microbiology*, Sep. 2005, pp. 5587-5589, vol. 71, No. 9.
James V. Rogers et al., "*Bacillus anthracis* Spore Inactivation by Fumigant Decontamination," *Applied Biosafety*, 2008, pp. 89-98, vol. 13, No. 2.
William A. Rutala et al., "Clinical Effectiveness of Low-Temperature Sterilization Technologies" *Infection Control and Hospital Epidemiology*, Oct. 1998, pp. 798-804, vol. 19, No. 10.
William A. Rutal et al., "Low-Temperature Sterilization Technologies: Do We Need to Redefine "Sterilization"?" *Infections Control and Hospital Epidemiology*, Feb. 1996, pp. 87-91, vol. 17, No. 2.
Daniel Spangler et al., "In Vitro Antimicrobial Actibity of Oxidized Regenerated Cellulose Against Antibiotic-Resistant Microorganisms," *Surgical Infections*, 2003, pp. 255-262, vol. 4 No. 3.
Volker Sigwarth et al., "Effect of Carrier Materials on the Resistance of Spores of *Bacillus stearothermophilus* to Gaseous Hydrogen Peroxide," *PDA Journal of Pharmaceutical Science and Technology*, 2003, vol. 57, No. 1.
Jarmila Vytrasova et al., "Antimicrobial effect of oxidized cellulose salts," *Journal for Industrial Microbiology Biotechnology*, Aug. 2008, pp. 1247-01252, vol. 35.
C. M. Yakacki et al., "Cytotoxicity and thermomechanical behavior of biomedical shape-memory polymer networks post-sterilization," *Biomedical Materials*, Feb. 2, 2008, pp. 1-9.

* cited by examiner

STERILIZATION SYSTEM AND DEVICE

The present application is a Continuation-In-Part of PCT/US2005/000173, filed on Jan. 6, 2005, the contents of which are incorporated herein by reference in their entirety. PCT/US2005/000173 relies for priority on U.S. provisional application No. 60/534,395 filed on Jan. 7, 2004; U.S. provisional application No. 60/575,421 filed Jun. 1, 2004; and U.S. provisional application No. 60/564,589 having a filing date of Jul. 23, 2004, each of which are incorporated herein by reference in their entirety. The present application is related to U.S. Provisional Application No. 60/542,298, filed Feb. 9, 2004, which is incorporated herein by reference in its entirety.

FIELD OF THE INVENTION

This invention relates to sterilization devices and methodologies using nitric oxide and/or other oxides of nitrogen as the sterilant. Specifically, the invention relates to a device and method that uses nitric oxide and/or additional oxides of nitrogen for sterilization purposes.

BACKGROUND OF THE INVENTION

Steam autoclaving is the hospital standard for sterilizing most medical instruments. This method exposes materials to steam at 121° C. at 15-20 lbs per square inch of pressure for 15-30 minutes. Killing is mediated by heat denaturation of proteins, DNA, and subsequent interruption of metabolic functions. The method requires cumbersome equipment, a power supply and plumbing, although benchtop models have fillable water tables. Aside from these logistical problems, autoclaving is not suitable for many plastics and other heat labile materials.

Sterilant gases can kill or control the growth of microbial contaminations. Some of these sterilant gases include chlorine dioxide, sulfur dioxide, hydrogen peroxide, nitric oxide, nitrogen dioxide, carbon dioxide, hydrogen sulfide, ozone and ethylene oxide. One problem with many of the sterilant gases is that they are explosive in high concentrations (e.g. ethylene oxide, hydrogen peroxide, chlorine dioxide). Thus, storing, containing and using these gases in high concentrations represent a hazard to the user. For safety reasons, this limits the usable concentration of gas and creates an additional disadvantage. The concentration of the sterilant gas must be decreased due to safety concerns, while the exposure time must be increased to achieve effective sterilization.

Certain sterilant gases, such as chlorine dioxide, ozone and hydrogen peroxide are difficult and expensive to transport. Many of these sterilant gases are powerful oxidizers. Oxidizing gases are expensive and paperwork intensive to ship in bulk tanks, further complicating their use. Gases, such as ozone and chlorine dioxide, must be generated at or near the point of use. On-site plants for generating one such sterilant gas, chlorine dioxide, are costly and require significant space to implement.

Hamilton U.S. Pat. No. 6,607,696 describes a device for delivering chlorine dioxide to disinfect or sterilize a liquid or an item contained in the liquid. The device uses a permeable sachet containing gas generating reactants, such as sodium chlorite and citric acid, where the sachet is a receptacle permeable to liquid and gas. Liquid can diffuse into the receptacle to reach the gas generating reactants that then generate a gas, such as chlorine dioxide. The gas that diffuses out of the permeable sachet is not sealed from the environment/atmosphere. Multi-compartmental devices that employ gas-generating ingredients contained in closed compartments that are permeable and permit the diffusion of liquids and gases through the compartments to produce chlorine dioxide, such as the sachet and envelope compartments used in U.S. Pat. Nos. 6,602,466 and 6,607,696. Not only are these systems expensive and difficult to manufacture, but they do not contain the generated gases in a manner that prevents their unintended escape to the environment/atmosphere nor do they allow the user to predictably and controllably release the gas into a sealable container that is sealed when the contents are sterilized.

Thus, there is a need for methods and devices that generate sterilant gases at the point of use in a safe and efficient manner. There is a further need for processes capable of producing significant concentrations of sterilant gas without the danger of explosion or oxidative fire. There is a need to produce greater concentrations of NO in a short time period to allow a shorter exposure and make the sterilization process more efficient. There is also a need for a system and method to generate small amounts of sterilant gas in an economical manner. The ability to economically generate small amounts of sterilant gases allows for easy transportation of the sterilizing system, imparting portability to the system not commonly found with traditional sterilization devices and methods.

Given the problems with traditional gaseous sterilants and disinfectants, there is a need for a sterilant gas generating system and method where the risk of explosion and oxidative fire is minimized, that produces the sterilant gas rapidly, safely, economically, and in a scaleable manner. There is also a need for a sterilant gas that can be safely used at high enough concentrations to minimize the time required for sterilization or disinfecting. Also, there is a need for a sterilant gas that does not significantly alter or destroy the materials and/or objects being sterilized, such as by altering the molecules of the materials being sterilized or changing the structural form of the object or material.

SUMMARY OF THE INVENTION

The present invention provides a method to generate and use one or more oxides of nitrogen for the purpose of sterilization and disinfecting. These oxides of nitrogen may include: nitric oxide, nitrogen dioxide, dinitrogen tetroxide or additional oxides of nitrogen individually or in combination. By using compounds that generate nitric oxide on acidification, and combining the nitric oxide with ambient air within an exemplary device, the method generates both water soluble and lipid soluble oxides of nitrogen each of which possess anti-microbial properties on their own. In addition, the mixture of gases generated in the present invention has lower oxidation potential than other sterilant gases, making them safer to handle. Furthermore, the mixture of gases lacks the potential for explosive hazard possessed by many currently favored sterilant gases.

Figure 1:
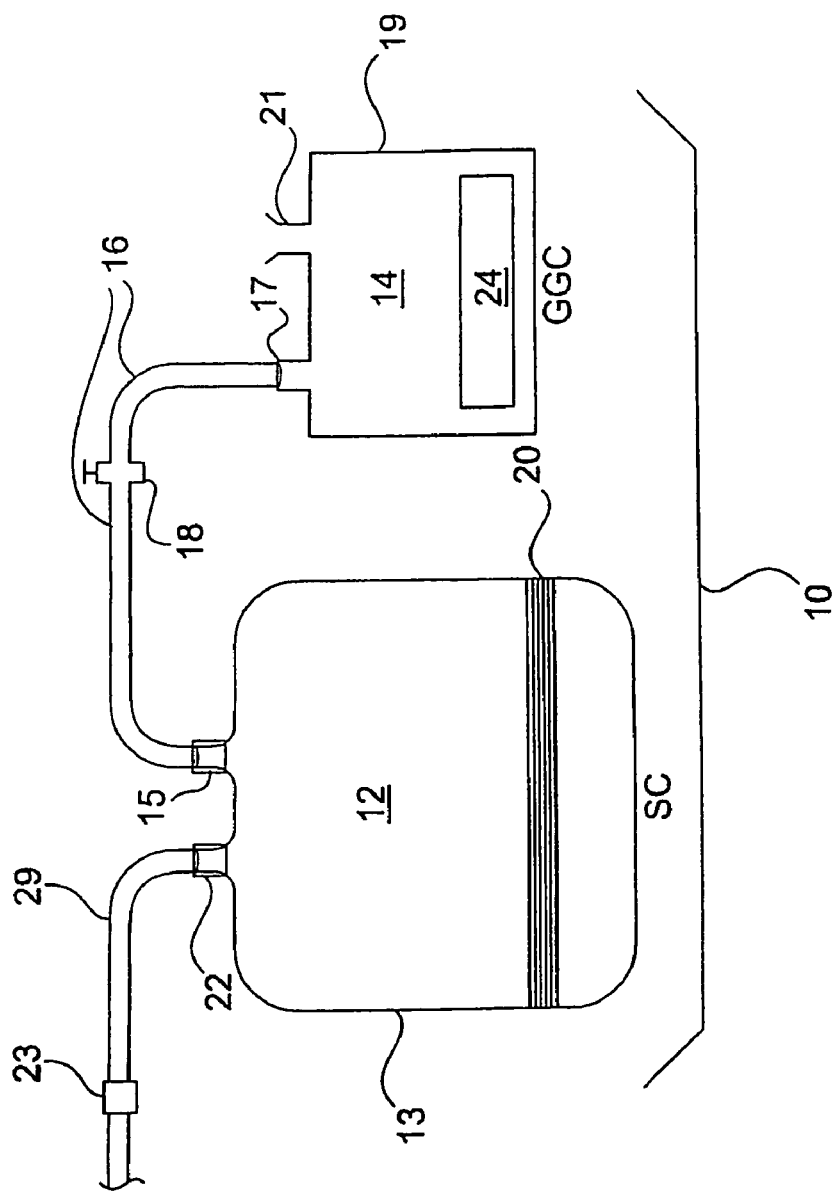
FIG. 1 shows a sterilization device having a sterilization chamber (SC) 12, a gas generation chamber (GGC) 14, and a connecting tube 16 having a safety valve 18. The SC 12 has a closure 20, a connecting port 15, and an exhaust port 22 that attaches to exhaust tubing 29. An exhaust valve 23 is attached to the exhaust tubing 29. The GGC 14 contains the composition capable of generating a sterilant gas (sterilant gas-generating composition) 24. The GGC 14 has a fitting 17 to which connecting tubing 16 is attached, and a filling port 21 for adding liquids.

The foregoing features of the invention are more readily understood by reference to the following detailed description.

DETAILED DESCRIPTION OF THE INVENTION

The present invention provides methods and devices that generate or use nitric oxide, along with other oxides of nitrogen, to sterilize or disinfect instruments, devices, materials, tools and equipment that must be sterile, typically for medical applications. The use of nitric oxide alone, or in combination with oxides of nitrogen that form in combination with air, as a disinfectant and sterilant gas mixture has several advantages over other gases. Neither nitric oxide nor other oxides of nitrogen are explosive at high concentrations. In addition, because nitric oxide and other oxides of nitrogen have a weaker oxidizing potential than peroxides and ozone, they allow for a broader list of materials that can be sterilized. Another advantage to using nitric oxide and/or other nitrogen oxides is that their density is closer to that of air, and thus do not settle to the bottom of a closed compartment when mixed with air, as would chlorine dioxide, which is greater than twice the density of air.

Generating a mixture of the oxides of nitrogen can have additional advantages over pure nitric oxide and other single entity sterilization gases. Nitric oxide is very lipid soluble and has the ability to disrupt the lipid membranes of microorganisms. Furthermore nitric oxide may inactivate thioproteins thereby disrupting the functional proteins of microbes. Nitrogen dioxide is more water soluble than nitric oxide. Finally, nitric oxide and nitrogen dioxide are extremely effective disruptors of DNA, causing strand breaks and other damage leading to an inability for the cell to function.

A mixture of nitric oxide and air will react, resulting in a mixture containing many different oxides of nitrogen. Specifically, the addition of NO to air, or air to NO, results in the formation of $NO_2$ when NO reacts with the oxygen in air. The concentration of each nitrogen-oxide species that is present in a mixture will vary with temperature, pressure, and initial concentration of the nitric oxide.

DEFINITIONS

As used herein, the term "gas" or "gases" means any matter that is not in the solid state or liquid state, but rather, has relatively low density and viscosity, expands and contracts greatly with changes in pressure and temperature, diffuses readily and has the tendency to become distributed uniformly throughout any container.

As used herein, the term "nitric oxide" or "NO" means the NO free radical or NO.. As used herein, the term $NO_x$ is an abbreviation for nitrogen oxides or the oxides of nitrogen, which are the oxides formed by nitrogen in which nitrogen exhibits each of its positive oxidation numbers from +1 to +5. As used herein, the terms "nitrogen oxides" and 'oxides of nitrogen' and '$NO_x$' mean a gas having one or more of the following gases, all of which contain nitrogen and oxygen in varying amounts: nitric oxide (NO) nitrogen dioxide ($NO_2$), nitrogen trioxide ($NO_3$), dinitrogen trioxide ($N_2O_3$), dinitrogen tetroxide ($N_2O_4$), dinitrogen pentoxide ($N_2O_5$) and nitrous oxide ($N_2O$). Examples of preferred sterilant gases include, but are not limited to NO, $NO_2$, $NO_3$, $N_2O_3$, $N_2O_4$, $N_2O_5$, $N_2O$ and mixtures thereof. Examples of the most preferred sterilant gases are NO, $NO_2$, $N_2O_4$ and mixtures thereof.

As used herein, the term "NO-generating" compound or composition means a compound or composition capable of producing or releasing NO, $NO_2$, and $NO_x$. As used herein, the term "sterilant gas-generating" compound or composition means a compound or composition capable of producing or releasing a sterilant gas. An NO-generating compound is one type of sterilant gas-generating compound. The preferred sterilant gas-generating compounds used in the systems, devices and methods of the present invention are carbon-based diazeniumdiolate compounds that generate at least 1 mole of NO per mole of compound.

As used herein, the term "sterilization chamber" means any gas tight chamber of any size, whether comprised of hard or soft materials, where items to be sterilized or decontaminated can be contained. Preferably, the sterilization chamber is capable of (i) maintaining a vacuum; (ii) receiving a sterilizing gas; and (iii) receiving air. Sterilization is a high-level of decontamination that destroys all microbial life, including highly resistant bacterial endospores. Disinfection in an intermediate-level of decontamination, which eliminates virtually all pathogenic microorganisms, with the exception of bacterial spores. As used herein, the terms "sterilize" "sterilizing" and "sterilization" mean the killing or removal of all microorganisms in a material or on an object. When a material or object is "sterilized" or "sterile" there are no living organisms in or on a material or object. Since sterilization eliminates all microorganisms, including endospores, a method, system and/or device that sterilizes a material or object, therefore, also disinfects and decontaminates the material or object. As used herein, the term "object" refers not to a feature of the invention, but rather to the article or material being acted upon to be sterilized and/or decontaminated by the disclosed sterilizing methods, systems and devices. The term "object" can also include a material to be sterilized, no matter the physical form. An object may include, for example, without limitation, a medical device or medical instrument or any other article or combination of articles for which sterilization is desired. An object may have a wide variety of shapes and sizes and may be made from a variety of materials (e.g., without limitation, metal, plastic, glass).

As used herein, the term "gas generation chamber" means any container, of any size or composition, which may be used to contain a gas and/or a gas-generating compound. Preferably, the gas generating chamber is made of a material that is impermeable to liquid and impermeable to gas. As used herein, the term "microbe" means any bacteria, virus, fungi, parasite, mycobacterium a or the like. As used herein, the term "scrubbing" means the removal or conversion of toxic oxides of nitrogen from the exhaust stream of the sterilization device.

As used herein, the term "medical device" means any instrument, apparatus, implement, machine, appliance, contrivance, implant, or other similar or related article, including any component, part, which is intended for use in the cure, mitigation, treatment, or prevention of disease, of a human or animal, or intended to affect the structure or any function of the body of a human or animal; and, which is intended to be inserted, in whole or in part, into intact tissues of a human or animal. As used herein, the term "implant" or "implantable" means any material or object inserted or grafted into intact tissues of a mammal.

As used herein, the term "impermeable" means a substance, material or object that prohibits over 95% of any liquid or gas from passing or diffusing through it, for at least one hour. As used herein, the term "permeable" means a substance, material or object that allows the passage of gases and/or liquid through it.

The sterilization system and method of the present invention utilizes one or more oxides of nitrogen (individually or in combination) to sterilize a wide variety of devices, instruments, materials, human and animal tissues, drugs, biologicals, and a variety of medically relevant materials.

An additional sterilization system and method of the present invention employs compounds that release a sterilant gas, preferably nitric oxide, upon acidification. The system and method of the present invention generates nitric oxide that is used, typically as a mixture of water soluble and lipid soluble nitrogen oxide gases, to sterilize a wide variety of devices, instruments, materials, human and animal tissues, drugs, biologicals, and a variety of medically relevant materials. In one embodiment of the present invention, the object to be sterilized is made of a material that is used in health related products. Examples of health related products are, without limitation, all types of surgical instruments; cardiac surgery products; cardiac implants; cardiovascular stents; vascular implants; orthopedic surgery products such as surgical instruments, bone graft, bone scaffold; orthopedic implants; dental surgery products; dental implants; gastrointestinal implants, urinary tract implants; wound healing products; tissue engineering products. In another embodiment of the present invention, the tissue engineering product is a protein.

Typically, an object that is a medical device contains one or more materials, such metals, a non-metals, a polymers or plastics, an elastomers, as well as biologically derived materials. Preferred metals used in medical devices are stainless steel, aluminum, nitinol, cobalt chrome, and titanium. Examples of nonmetals are glass, silica, and ceramic.

In another embodiment of the present invention, the object to be sterilized is made of a material that is a polymer such as a polyester bioresorbable polymer, for example, without limitation, Poly(L-lactide), Poly(DL-Lactide), 50/50 Poly(DL-lactide-co-glycolide), Poly(e-caprolactone), mixtures thereof. Preferably, the material is a bioresorbable polymer capable of being used as an implant material and for drug delivery. Preferred polymers used in medical devices are polyacetal, polyurethane, polyester, polytetrafluoroethylene, polyethylene, polymethylmethacrylate, polyhydroxyethyl methacrylate, polyvinyl alcohol, polypropylene, polymethylpentene, polyetherketone, polyphenylene oxide, polyvinyl chloride, polycarbonate, polysulfone, acrylonitrile-butadiene-styrene, polyetherimide, polyvinylidene fluoride, and copolymers and combinations thereof. Other materials found in medical devices are polysiloxane, fluorinated polysiloxane, ethylene-propylene rubber, fluoroelastomer and combinations thereof. Examples of biologically derived materials used in medical devices include, without limitation, polylactic acid, polyglycolic acid, polycaprolactone, polyparadioxanone, polytrimethylene carbonate and their copolymers, collagen, elastin, chitin, coral, hyaluronic acid, bone and combinations thereof.

Certain types of medical devices and implants include a bioactive coating and/or biocompatible coating, examples of which are, without limitation, infection resistance coating, antimicrobial coating, drug release coating, anti-thrombogenic coating, lubricious coating, heparin coating, phosphoryl choline coating, urokinase coating, rapamycin coating, and combinations thereof. The bioactive coating can be a hydrophilic or hydrophobic coating. Further examples of bioactive coatings and polymers include, but are not limited to polyvinyl pyrrolidone, polyethylene glycol, polypropylene glycol, polyethylene glycol-co-propylene glycol, polyethylene glycol acrylate, polyethylene glycol diacrylate, polyethylene glycol methacrylate, polyethylene glycol dimethacrylate, polyethylene oxide, polyvinyl alcohol, polyvinyl alcohol-co-vinylacetate, polyhydroxyethyl methacrylate, and polyhyaluronic acid, and hydrophilically substituted derivatives, monomers, unsaturated pre-polymers, and uncrosslinked polymers with double bonds thereof. Addition bioactive coatings and polymers are polytetrafluoroethylene, polyethylene, polypropylene, poly(ethylene terephthalate), polyester, polyamides, polyarylates, polycarbonate, polystyrene, polysulfone, polyethers, polyacrylates, polymethacrylates, poly(2-hydroxyethyl methacrylate), polyurethanes, poly(siloxane)s, silicones, poly(vinyl chloride), fluorinated elastomers, synthetic rubbers, poly(phenylene oxide), polyetherketones, acrylonitrile-butadiene-styrene rubbers, polyetherimides, and hydrophobically substituted derivatives thereof and their precursor monomers.

In another embodiment of the present invention, the object to be sterilized is made of a material that is a bioabsorbable polymer or a drug-bearing or drug-eluting polymer or a mixtures thereof. In a preferred embodiment of the present invention, the object to be sterilized is an implant.

A preferred embodiment of the system and method of the present invention generates the gases at the point-of-use. Such point-of-use methods, systems and devices eliminate the need for heavy tanks of potentially hazardous gases or expensive on-site gas generation plants. The point-of-use gas generation employed in the system and method of the present invention can be functional without requiring electricity, which allows the method to be adapted for portable embodiments for sterilization, disinfecting, and decontamination in austere environments such as combat areas, refugee camps, etc. In one aspect, the present invention describes a method to generate a mixture of nitrogen oxides for sterilization and disinfecting purposes. The method requires an apparatus that integrates the gas generation and delivery method. The apparatus used in the process may have many potential embodiments.

In a preferred embodiment of the system or device of the present invention, a sterilization chamber is used, along with a source of the sterilant gas comprised of one or more oxides of nitrogen. The sterilization chamber may be in fluid connectivity with the source of the sterilant gas; alternatively, the source of the sterilant gas can be within the sterilization chamber. One preferred embodiment includes a gas generation chamber in fluid connectivity with a sterilization chamber. Another preferred embodiment has the gas generation chamber contained within the sterilization chamber.

Also preferred, are embodiments of the system and method of the present invention that produces a mixture of nitrogen oxides having less oxidative potential than commonly used sterilant gases, including ozone and hydrogen peroxide. An additional advantage is that the mixture of nitrogen oxides produced has much less explosive potential than the commonly used sterilant gases, including ethylene oxide, hydrogen peroxide, and chlorine dioxide. This allows the use of greater concentrations of the gaseous mixture the system and method of the present invention thereby allowing less exposure time in the sterilization cycle as known to those skilled in the art.

Yet another advantage is that the method of the present invention is the generation of multiple chemical species with different chemical properties for the purpose of sterilization and disinfecting. Those skilled in the art understand that multiple mechanisms of cell killing or deactivation are often preferred over single mechanisms of action. Antimicrobial agents with different mechanisms of action are often synergistic, producing a greater effect than would be expected by simply adding the effects from each agent together. The same principle is applied to microbial resistance, where multiple, distinctly acting agents are used for treatment.

In one preferred embodiment of the method and system of the present invention, NO gas is generated using the class of nitric oxide donors known as diazeniumdiolates. These compounds spontaneously release NO in solution, with rates that are proportional to the acidity of the solution. Highly acidic conditions can be used to generate NO in the method of the present invention, generate NO gas rapidly (complete theoretic release of NO in <30 sec).

A preferred embodiment of the method and system of the present invention uses carbon-based diazeniumdiolates rather than nitrogen-based compounds. Carbon-based diazeniumdiolates are preferred because nitrogen-based compounds are able to form highly carcinogenic nitrosamine species, as described by Parzuchowski et al., J Am Chem. Soc 124: 12182-91 (2002). Also preferred are carbon-based diazeniumdiolate compounds that release large amounts of NO such as but not limited to those described in U.S. Provisional Pat. Appl. 60/542,298, (which produces greater amounts of nitric oxide per mole of compound, as compared to the compounds disclosed in U.S. Pat. No. 6,232,336) and U.S. Provisional Pat. Appl. 60/542,298, filed Feb. 9, 2004, which is incorporated herein by reference in its entirety. Another embodiment of the methods and devices of the present invention employs a sterilant gas-generating composition that includes a nitrogen-based diazeniumdiolate compound.

In a preferred embodiment of the methods and devices of the present invention that employ a sterilant gas-generating composition that includes a carbon-based diazeniumdiolate compound, the carbon-based diazeniumdiolate compound produces quantities of NO that are greater than 1 mole of NO per mole of the carbon-based diazeniumdiolate compound. In yet another embodiment of the methods and devices of the present invention, the carbon-based diazeniumdiolate has a carbon bearing a diazeniumdiolate group, wherein the carbon does not comprise part of an imidiate, thioimidate, amidine or enamine.

In yet another embodiment of the methods and devices of the present invention, the carbon-based diazeniumdiolate compound has the formula:

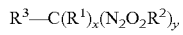
$R^3—C(R^1)_x(N_2O_2R^2)_y$ wherein x is an integer from 0 to 2 and y is an integer from 1 to 3 and the sum of x plus y equals 3;

wherein $R^1$ is not an imidiate, thioimidate, amidine or enamine;

wherein $R^2$ is selected from the group consisting of a countercation and a protecting group on the terminal oxygen; and wherein $R^3$ is a phenyl group.

In yet another embodiment of the methods and devices of the present invention, the carbon-based diazeniumdiolate compound has the formula:

wherein $R^1$ is not an imidiate, thioimidate, amidine or enamine;

wherein $R^2$ is selected from the group consisting of a countercation and a protecting group on the terminal oxygen; and wherein $R^3$ is a phenyl. In a preferred embodiment of the invention, $R^1$ is selected from the group consisting of an electron withdrawing group, a nitro group, an ether, a thioether, and a non-enamine amine;

wherein the $R^2$ substituent is selected from the group consisting of aliphatic, aromatic, and non-aromatic cyclic groups; and wherein the $R^3$ substituent is selected from the group consisting of mono- or di-substituted amino, unsubstituted amino, ammonium, alkoxy, acetoxy, aryloxy, acetamide, aldehyde, benzyl, cyano, nitro, thio, sulfonic, vinyl, carboxyl, nitroso, trihalosilane, trialkylsilane, trialkylsiloxane, trialkoxysilane, diazeniumdiolate, hydroxyl, halogen, trihalomethyl, ketone, benzyl, and alkylthio. The countercation is selected from the group consisting of an ammonium and other quaternary amines; and further wherein the protecting group is selected from the group consisting of aryl, sulfonyl, glycosyl, acyl, alkyl and olefinic groups.

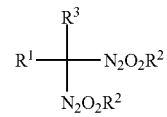

One NO-generating compound that may be used in the method and system of the present invention, though with caution, is sodium nitroprusside because of its concurrent formation of cyanide in the gas generation chamber. The formation of cyanide represents a human health hazard and creates a disposal safety issue for the gas generation chamber. Nitrosothiols may also be used to generate NO in the current invention, however nitrosothiols have the tendency to reform after they have released NO, thus creating a chemical sink for NO and making the release of NO unpredictable. A sterilant gas-generating composition of the present invention, therefore, may include a nitrogen-based diazeniumdiolate compound, such as a nitrosothiol, S-nitrosoglutathione, sodium nitroprusside, molsidomine, an iron-sulfur nitrosyl, Roussin's black salt, and mixtures thereof.

A most preferred embodiment of the system and method of the present invention, the NO-releasing compound employed is a carbon-based diazeniumdiolate compound. Carbon-based diazeniumdiolate molecules release a greater amount of nitric oxide and do not form nitrosamines. Preferably, the carbon-based diazeniumdiolate compound produces greater quantities of NO per mole. Preferably, a C-based diazeniumdiolate compound that is capable of producing at least one mole of NO per mole of diazeniumdiolate is used as the sterilant gas generating compound is used in the system and method of the present invention. Such a carbon-based diazeniumdiolate is described in U.S. provisional patent application 60/542,298 entitled "Nitric Oxide-Releasing Molecules" filed Feb. 9, 2004; the entirety of which is hereby incorporated by reference.

The system and method of the present invention preferably uses a C-based diazeniumdiolate compound that does not result in the formation of carcinogenic nitrosamines when acidified. Another advantage of using a C-based diazeniumdiolate compound as the preferred NO-releasing compound is that it releases a greater quantity of NO per mole of NO-releasing compound. For example, nitrogen-based diazeniumdiolates and nitrosothiols produce lower quantities of NO per mole compound when compared to the carbon-based diazeniumdiolate compounds. Also, the use of a C-based diazeniumdiolate compound as the preferred NO-releasing compound allows the use of an acid to release NO rather than the copper solution required for release of NO from nitrosothiols. Yet another advantage of the method and system of the present invention is that it has a reduced environmental impact as compared to a method requiring a solution containing copper ions.

The nitric oxide generating compounds utilized in the system and method of the present invention provide several advantageous elements to the present invention. One advantage is that nitric oxide has a high degree of lipid solubility, making it toxic to almost all microbes, which have lipid membranes (the exception is non-enveloped viruses).

Nitrogen dioxide, and other oxides of nitrogen such as dinitrogen tetroxide, are more water soluble than nitric oxide. These, and especially nitrogen dioxide, are highly damaging to DNA, resulting in nitrosation and deamination of DNA bases and single and double strand breaks. Damage to DNA is a powerful killing mechanism. Combined, the mixture of gases in the present invention provides a multi-pronged attack of microbes through a variety of possible mechanisms of action. The antimicrobial benefits of a method that uses multiple mechanisms of action, as discussed above.

Yet another advantage to the system and method of the present invention is that it can permit the formation of small amounts of nitrous acid and nitric acid in the water that attaches to solids in humid environments, which can enhance the antimicrobial properties of the present invention.

Another embodiment of the system and method of the present invention uses a gas generating chamber that is a pressurized or non-pressurized cylinder containing one or more oxides of nitrogen. Though this embodiment sacrifices portability, it is useful in large scale decontaminations, such as military or other very large equipment. The one or more oxides of nitrogen may be stored at high concentrations within the cylinder. Although this embodiment is less desirable due to the hazard and added costs and paperwork involved with shipping of concentrated pressurized gases. A more preferred method would be to dilute the concentration of the one or more oxides of nitrogen within the cylinder to a desired concentration by mixing with nitrogen or other inert gas including, but not limited to, argon, helium, and neon. The gas or gas mixture can be delivered to the sterilization chamber through a metered regulator in fluid connectivity with the sterilization chamber, or other gas delivery method known to one skilled in the art. Another embodiment includes computer or microprocessor means to control the delivery of sterilant gas from the gas cylinder.

In embodiments of the present invention where the NO-releasing entity is activated by acid, any acid can be used to generate NO. In one embodiment of the present invention the NO donors are activated by the addition of a liquid activator that is an aqueous acid, as described in Example 1. The liquid activator may be, for example without limitation, water, an acid, and mixtures of water and acids. Due to the inconvenience of handling and transporting aqueous acids, powdered acids that are activated by water are preferred. While any powdered acid would be acceptable, powdered acids with low pKa are preferred because the preferred method is to rapidly generate the NO, and low pKa acids are more effective. These low pKa acids include but are not limited to oxalic and maleic acids. Generally, up to ten-fold molar excess of powdered acid is used, however lower molar ratios may also be acceptable.

A preferred embodiment of the system and method of the present invention includes a gas generation chamber containing both a carbon-based diazeniumdiolate and a powdered acid, whereby the gas generation chamber includes a rapidly sealing opening that allows the addition of a liquid, preferably water, and is in fluid connectivity with the sterilization chamber so that gas generated upon activation of the carbon-based diazeniumdiolate is transported into the sterilization chamber. Additional connections and/or ports may be included for such purposes as to apply a vacuum, if necessary, to release NO gas from the chamber. Preferably, the NO gas is released into a reusable $NO_x$ scrubbing system. Preferred methods and devices of the present invention include the scrubbing of the sterilant gas after the object is sterilized.

A desiccant may be included in the gas generation chamber to reduce moisture during manufacture, shipping, and storage of the gas generation chamber. Examples of desiccants may include but not be limited to molecular sieves, silica gels, and other methods known to one skilled in the art. Care should be taken that the amount of desiccant does not prevent the generation of NO on the addition of water.

One skilled in the art can apply The Ideal Gas Law, the moles of NO released from the various NO-releasing compounds, the molecular weight of the compound in question and derive the weight of the compound necessary in the gas generation chamber to achieve a desired percent of NO added to any specified volume that comprises the sterilization chamber. For example, 1.956 grams of an NO-releasing compound that generates 2 moles of NO per mole of compound having a molecular weight of 163 gms/mole is used to produce 0.0225 moles of NO and provide a concentration of 50% NO in a one liter volume. This allows the user to control the amount of NO added for various sterilization applications. For example, medical practitioners may desire a more rapid sterilization cycle, requiring higher concentrations of added NO. Those users who are more concerned with portability may be less sensitive to speed and cost of the process. Longer sterilization cycles may require less of the NO-releasing compound, i.e., less NO added. Thus, the device 100 and process offer the flexibility to provide potential end users with options regarding cost, speed, portability, and other utilization parameters.

In one embodiment of the present invention, a lightweight, portable device employing chemically generated NO as a rapid, effective sterilant which requires no electrical power so that it can be used in austere environments.

DETAILED DESCRIPTION OF THE INVENTION

FIG. 1 shows the device 10 in its most simplistic form. The device 10 is comprised of the subcomponents that include the sterilization chamber (SC) 12, the gas generation chamber (GGC) 14, a connecting tube 16 that allows gas to flow from the GGC 14 to the SC 12, and a safety valve 18, along the length of the connecting tube 16 that separates the GGC 14 from the SC 12. The SC 12 has a closure 20, a connecting port 15, and an exhaust port 22 that attaches to exhaust tubing 29. An exhaust valve 23 is attached to the exhaust tubing 29. The GGC 14 contains the powdered sterilant gas-generation composition or compound 24, which is described in detail below. The GGC 14 is further comprised of a female lure fitting 17 to which the connecting tubing 16 is attached, and a filling port 21 for addition of liquids. Each subcomponent comprising the device 10 is described in greater detail below.

FIG. 1 also details the sterilization chamber (SC) 12. The SC 12 includes a physical container 13 comprised of a plastic, a closure 20, that is gas impermeable and allows re-opening and re-sealing of the SC 12 for loading and unloading of the materials to be sterilized, a connecting port 15 that allows a gas-tight seal with connecting tube 16, and an exhaust port 22 that allows the removal of the gaseous sterilant from the SC 12 prior to removal of the sterilized materials. The SC 12 can be comprised of any plastic material that can contain a low molecular weight gas for up to 45 minutes. Due to the short duration of the period during which it is necessary to contain the gas, semi-gas permeable materials may be used to construct the SC 12, allowing for optimization of weight, toughness, and cost parameters for each individual application.

Plastics used for the physical container 13 of the SC 12 may include highly chemical resistant polymers, such as but not limited to Styrene-ethylene-butylene modified block copolymer with silicone oil (for example, C-FLEX tubing), a fluoropolymer made from Halar resin (for example, Chemfluor 367), Ethylene Propylene Diene Monomer (EPDM), Ethylene TetrafluoroEthylene (ETFE), Polyvinylidene Fluoride (for example, Kynar), fluoropolymers (for example, MFA), polyketones or polyetheretherketones (PEEK), perfluoroalkoxy fluorocarbon (PFA), fluoroethylene-propylene (FEP), polyimide, and polyvinylchloride (PVC). The closure 20 may be located at a variety of locations in the SC, preferably, at a point on the SC 12 opposite from the connecting port 15 and the exhaust port 22, or towards either side of the SC 12. The closure 20 is preferably constructed from polyethylene. One preferred closure is one having interlocking linear fasteners that are resistant to pressure breaches, such as the U-MAXI-GRIP (Illinois Tool Works, Inc. Glenview, Ill.). While many interlocking linear fasteners are available, this model is particularly desirable due to its resistance to pressure breaches.

Figure 2:
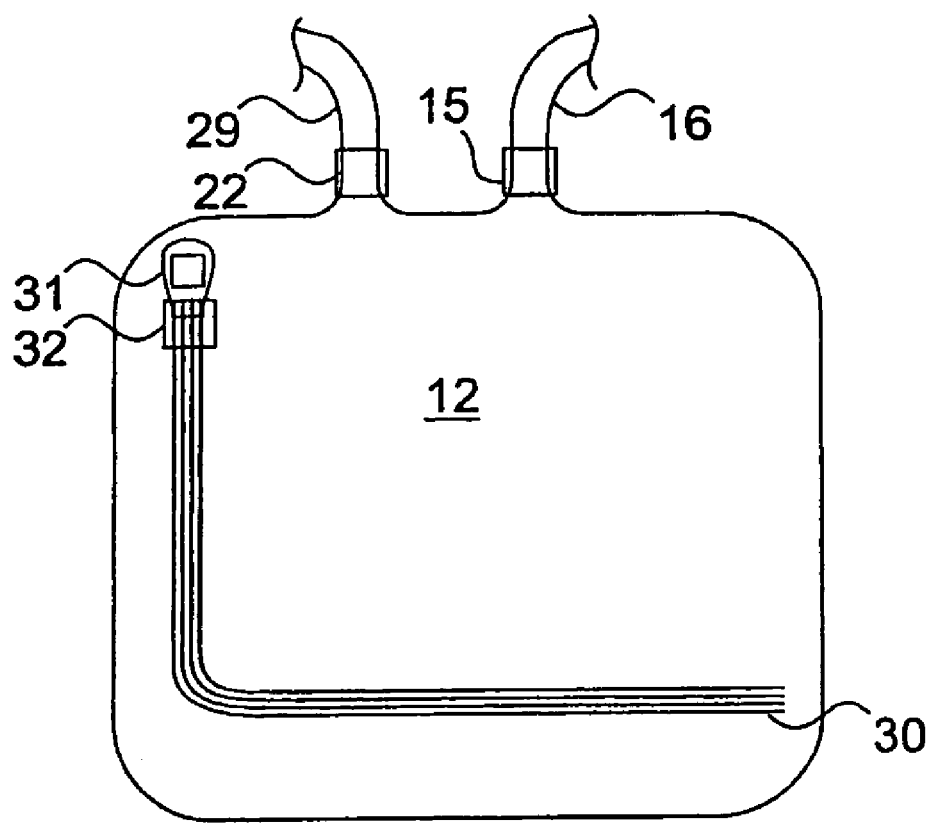
FIG. 2 is a drawing of another embodiment of the Sterilization Chamber 12 that has a flap closure 30 for opening or sealing the SC 12.

An alternate embodiment for the SC 12 is shown in FIG. 2, in which the SC 12 uses a flap closure 30 that is a C-shaped track of interlocking plastic hooks and ribs, sealed or opened by using a hinged zipper-like tab 31 and guide slot 32 that separates or compresses the interlocking components, resulting in the opening or sealing of the SC 12. The flap closure 30 is positioned 1 to 2 cm from the perimeter of the SC 12 over three contiguous sides of the SC 12, allowing for a flap of plastic from the SC 12 to be pulled back for easy loading and unloading of the SC 12.

The connection port 15 allows for a gas-tight connection between the SC 12 and the connecting tube 16. A preferred embodiment includes a female lure fitting 25 at the top of the connection port 15 whereby the end of the connecting tube 16 can be comprised of a male lure fitting 27 or a tapered shaft designed to snugly fit the female lure fitting 25. Alterations in the configuration are well within the skill of the art, such as having the lure fitting at the top of the connection port 15 be a male lure fitting and having the end of the connecting tube 16 be a female lure fitting.

In one embodiment, the exhaust port 22 is a plastic flange, that is a contiguous unit with the exhaust tube that flanges out from the SC 12 and tapers into a length of exhaust tubing 29. Exhaust tubing 29 is fitted with a valve 23 that, when closed, seals the SC 12 from the ambient air. In a preferred embodiment, the value 23 is a roller-activated compression valve is many possible embodiments for means to seal the exhaust tubing 29, known to those of skill in the art.

The connecting tube may be made of any flexible plastic that is relatively resistant to chemicals. Preferred plastic materials include, but are not limited to, C-FLEX, Chemfluor 367, EPDM, ETFE, Kynar, MFA, PEEK, PFA, FEP, polyimide, and PVC. The length of the connecting tube should be sufficient to allow the user to freely manipulate each chamber without disturbing the other chamber. Typically, a length of 20 to 30 inches of connecting tube 16 is preferred, however lengths outside the range of 20 to 30 inches are also functional. At either end of the connecting tube 16 there is a male lure fitting. Alternatively, there is a tapered hard plastic tip that can be inserted in the female lure fitting to insure a fluid-tight seal.

A broad range of safety valves 18 may be used to separate the GGC 14 from the SC 12 including, but not limited to, crimp valves, roller-activated compression valves, and the like. Any valve that can seal the flow of fluid from the GGC 14 to the SC 12. A preferred embodiment of the present invention employs an air-venting/vacuum breaking valve because it is self-activated.

Gas Generation Chamber (GGC) and Gas Generation Compound

The GGC 14 includes a container 19 that can be comprised of a variety of plastics that are chemically resistant. These may include but are not be limited to C-FLEX, Chemfluor 367, EPDM, ETFE, Kynar, MFA, PEEK, PFA, FEP, polyimide, PVC. In a preferred embodiment, the container is comprised of PFTE and/or polyolefins. The GGC 14 includes a female lure fitting 17 integrated for attachment of the GGC 14 to the connecting tube 16, which allows a contiguous flow of fluid from inside the GGC 14 to the SC 12. Preferably, the filling port 21 of the GGC 14 is a large, capped opening, which has a threaded rim protruding at least 0.5 cm above the wall of the GGC to allow easy grasping and capping.

Figure 3:
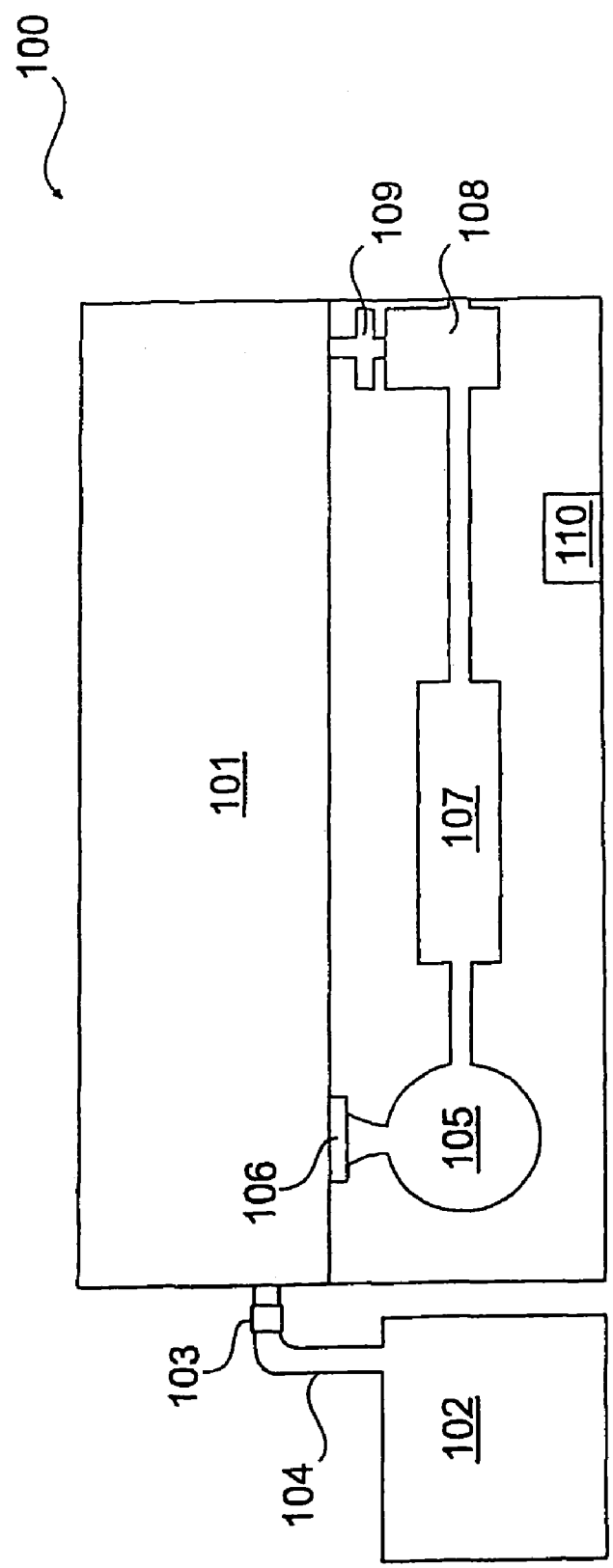
FIG. 3 is a schematic drawing of a sterilization device 100 of the present invention that is comprised of a hard casing with internal gas pumping and scrubbing functions.

Another embodiment of the present invention is presented schematically in FIG. 3. The sterilization device 100 includes a hard case with internal gas pumping and scrubbing means that is attached to a sealable gas generation chamber 102. The device 100 is in fluid connectivity with a gas generation chamber 102, through a sealable port 103. In a preferred embodiment, the sealable port 103 may be comprised of a double shut off quick disconnect coupling (Colder Products St. Paul, Minn.) where the tubing 104 from the gas generation chamber 102 has the male of female coupling and the sealable port 103 is comprised of the complimentary coupling. The advantage of the double shut off feature is that disconnection is possible without opening either the gas generation chamber 102 or the sterilization chamber 101 to the local environment. Thus, the sterilant gases are contained within the sterilization chamber 101, so that any residual gas from the gas generation chamber 102 remains contained until the scrubbing step.

The device 100 has a compartment that is comprised of an electronic or hand operated pump 105 that can be in fluid connectivity to the sterilization chamber 101, or not, depending on the position of an intake valve 106. The intake valve 106 may be manually operated, or microprocessor 110 controlled. The intake valve 106 allows the pump 105 to remove gas contained in the sterilization chamber 101 and the gas generation chamber 102 if it is in fluid connectivity with the sterilization chamber 101 at the time of pump activation. The gas is pumped through a scrubbing system 107 that deactivates and removes the gases from the exhaust stream. The compartment that comprises the inner lumens of the pump 105 and the scrubbing system 107 may or may not be fluid connectivity with the sterilization chamber 101 depending on the position of the intake valve 106. The device 100 is designed so that after completion of the sterilization cycle, activation of the valves and pump 105 draws gas from the sterilization chamber 101 through the intake valve 106 into the scrubbing system 107, through an exhaust valve 108 that directs the flow of gas out of the device 100, or back into the sterilization chamber 101 for the purpose of cycling the gas through the scrubbing system 107 for an additional period of time in order to reduce the levels of gas to OSHA or other regulating agency standards or guidelines. During such a recycling of gas, the gas that re-enters the sterilization chamber passes through a sterile air filter 109 to insure that any potential microbial contaminants picked up by the gas stream (in the pump 105, scrubbing system 107, and the necessary tubing to maintain fluid connectivity between the sterilization chamber 101 and these elements) does not enter the sterilization chamber 101 during the gas recycling process.

There are certain risks inherent with gaseous NO that require specialized delivery methods and handling procedures. Exposure to high concentrations of NO is hazardous. The Occupational Health and Safety Administration (OSHA) has set the current level of NO that poses an Immediate Danger to Life and Health at 100 parts per million (ppm) for a maximum of thirty minutes before the effects of exposure would pose a threat to health or life. OSHA has also set the levels of NO in the workplace at 25 ppm time weighted average for eight hours. Because of the dangers of potentially lethal doses of NO, any device or delivery system must include features to prevent the leakage of NO into the surrounding environment in a manner and at levels that may raise a risk that the leaked NO might be inhaled or otherwise applied to subjects that may be harmed by such exposure. The formation of nitrogen dioxide also represents a severe health hazard. OSHA limits for $NO_2$ are 1 ppm time weighted average over eight hours.

The system of the present inventions limits the user's exposure to the gases. The system and methods of the present invention include a system that can remove and/or detoxify the sterilant gases, otherwise known as scrubbing. The method of the present invention preferably includes a scrubbing process that removes and detoxifies these gases, prior to retrieving the sterilized or disinfected materials from the sterilization chamber. The scrubbing process, includes numerous methods for removing and detoxifying the NO, $NO_2$, and $NO_x$. Scrubbing systems and processes may employ an adsorbent to trap NO, and an oxidizer to convert NO to $NO_2$. In appropriate conditions, the sterilant gas may be exhausted to the outside environment, where the concentrations of NO, $NO_2$, and NO will dissipate easily. The scrubbing process may be achieved using a commercially available scrubbing device, such as the Buchi Analytical B-414 (New Castle, Del.). Ideally, the scrubbing device reduces the levels of NO, $NO_2$, and $NO_x$ in the exhaust gas to levels below the OSHA LTWA. Also, see, Basile R. Dealing with Nitrogen Oxide Emissions. http://www.finishers-management.com/may2002/nox.htm. It is also preferred that the method act rapidly.

The method of the present invention most preferably does not expose the user to concentrations of NO, $NO_2$, and/or NO that are above the OSHA limits. In a preferred embodiment, the gases are removed from the chamber prior to opening the chamber. In some instances such as outdoor use, the chamber may be opened without prior removal of gases. In order to limit the exposure to the sterilant gases, the system and method of the present invention include a system that can remove or detoxify the sterilant gases, otherwise known as scrubbing.

Examples 2, 3 and 4 describe embodiments of effective scrubbing systems that use Purakol and Purafil Select (Purafil, Doraville, Ga.). One skilled in the art will realize that many Configurations of a scrubbing system for a mixture of oxides of nitrogen can be designed.

In one embodiment of the present invention, the sterilization system is lightweight, requires no electrical (including battery) power, and can be completely self-contained. The core of the system of a re-usable, sealable sterilization chamber, a disposable gas generation chamber, and connecting tubing. The re-usable sterilization chamber can be loaded with surgical instruments or other materials to be sterilized, sealed, and connected to the gas generation chamber which is pre-filled with nitric oxide (NO) donors and acidic activators. Water is then added to the gas generation chamber, the chamber is sealed, and the generated gas flows into the sterilization chamber. A gas permeable, liquid impermeable valve separates the two chambers to avoid mixing the contents of the separate chambers. In one embodiment of the present invention, the sterilant gas-generating composition is capable of releasing sufficient quantities of NO to sterilize the object in as little as about 2 seconds to about 30 seconds. Carbon-based diazeniumdiolate compounds are capable of releasing sufficient quantities of NO to sterilize the object in as little as about 2 seconds to about 30 seconds. A duration of five minutes can be sufficient for sterilization, although a safety margin of an additional ten minutes is prudent.

Example 1

Sterilization with Varying Quantities of Delivered Nitric Oxide

A blood storage container (Nexell, Irvine, Calif.; Lifecell PL732 plastic tissue culture flask) is used as the sterilization chamber. Strips of stainless steel are dipped in $10^6$ CFU/ml sporulated *B. subtilis* var. *niger* (as determined by $ABS_{595}$ standardization curves). The strips are allowed to air dry, placed in the sterilization chamber, and then the sterilization chamber is heat sealed. The sterilization chamber is evacuated using a syringe and controlling air flow with the sterilization chamber valves. A known quantity of air is added to the vessel using a graduated syringe.

An NO-generating donor compound is placed in a 7 cc gas generation chamber. The gas generation chamber is attached to the storage container through luer lock connectors. The liquid activator, 3.0N HCl is added to the gas generation chamber and the generated gas is allowed to flow into the sterilization chamber. After a brief generation period, the gas is sealed in the sterilization chamber using a compression valve.

Varying quantities of NO gas, namely 10%, 5%, 2.5% and 1% NO, are tested for their efficacy in the sterilization chamber. The quantity (%) of NO gas generated and added to the sterilization chamber is calculated from the number of moles of NO required to be generated to result in the desired percentage of NO. This calculation uses the Ideal Gas Law and formula weight of the NO gas-generating compound, which in this Example is a diazeniumdiolate NO donor, to determine the mass of NO gas generating compound to be used.

All percentages tested, including 1%, are effective at killing $10^6$ CFU/ml sporulated *B. subtilis* var. *niger* in five minutes, as determined by culturing of the contaminated steel strips in LB at 37° C. and vigorous shaking for 48 hours, followed by plating onto agar plates. Controls are identically treated with the exception of the addition of percentages of nitrogen in place of NO. Control stainless steel strips exhibited visible growth after 24 hours of incubation under the stated conditions.

Example 2

Scrubbing of NO, $NO_x$ from a Portable Sterilization Chamber

After the sterilant gas is used in the sterilization chamber, the gas in the chamber is evacuated to another chamber containing scrubbing media. The evacuated gas is allowed to reside over the scrubbing media.

Two 300 ml PL732 tissue culture bags (Lifecell PL732 plastic tissue culture flask case, Nexell, Irvine, Calif.) are connected to each other with tubing. A hose clamp is used to close one bag off from the other. An incision is made in one bag, designated to be the 'scrubbing' bag, into which a premeasured amount of scrubbing media (6.0 to 60 grams of Purafil Select and Purakol in a 1:1 mixture) is added to the bag. The incision is then heat sealed. Both bags are evacuated with a syringe. Air (180 cc) is injected into the bag designated to be the sterilization chamber. Thereafter, 20 cc of NO gas is injected to reach a final concentration of 10% NO. The mixture of NO and air is allowed to remain in the sterilization chamber for 5 minutes. Thereafter, the hose clamp is removed and the sterilization bag is compressed to push all of the $NO_x$ gas into the scrubbing bag containing the Purafil Select and Purakol. The hose clamp is then secured. Immediately thereafter, samples (0.1 to 1.0 cc) of the atmosphere in the scrubbing bag are taken and injected into an NO detector, which measure the concentration of NO in parts per billion (ppb). Thereafter, 1.0 cc samples of atmosphere in the scrubbing bag are taken at timed intervals and injected into the $NO_x$ detector. Results of three successive trials are shown in Table 1. The scrubbing materials need not be changed between successive trials.

TABLE 1

Scrubbing of $NO_x$ gas

| Time minutes | Trial 1 [NO] ppb | Trial 2 [NO] ppb | Trial 3 [NO] ppb |
|---|---|---|---|
| 0 | 32556 | 69685 | 69094 |
| 5 | 686 | nd | 999 |
| 6 | nd | 1484 | Nd |
| 10 | 76 | nd | 253 |
| 12 | nd | 102 | Nd | nd = no data

Example 3

This example provides a method of scrubbing $NO_x$ by flowing the $NO_x$ gas through tubing filled with scrubbing media, which is connected to a container. Tubing (30 inches of ⅜ inch ID and inch OD silastic tubing) is filled with 13.3 grams of a 1:1 mixture of Purafil Select and Purakol. Some of the media is crushed in this process. Glass wool plugs are inserted in the ends of the tubing. Each end of the tube is connected to separate plastic tissue culture bag (Lifecell PL732 plastic tissue culture flask, Nexell, Irvine, Calif.). One bag includes an inline valve. The bags are evacuated of atmosphere and the valve is closed. One bag is designated the sterilization chamber, and injected with 180 cc of air and 20 cc of NO gas. The gas is allowed to remain in the sterilization back for five minutes. The valve is then opened and the gas pushed through the tubing into the receiving bag. A 0.5 cc sample of the atmosphere in the receiving bag is injected into the $NO_x$ detector. The results show that the contents of the receiving bag is 30 ppb $NO_x$, a concentration well below the OSHA guidelines.

Example 4

Scrubbing of NO, $NO_x$ from Sterilization Chamber

A sealable case (Pelican Products, Inc., Torrance, Calif.) is modified with additional ports comprised of EFC 12 Series Quick Disconnect Couplings (Colder Products Company, St. Paul, Minn.) and a plastic shelf with a self-sealing gasket edge which divided the case into upper and lower sections of approximately equal volume. The upper section is the sterilization chamber, which has a volume of 20.3 liters (4.5 in by 19 in by 14.5 in). One port into the sterilization chamber is used to introduce a known amount of NO gas into the sterilization chamber, and optionally, allowing for a recirculating flow. An exhaust port on the opposite end of the case is in the disconnected (sealed) state for the steps involving the addition of NO gas and during the 5 minute time period to approximate sterilization cycle time.

The lower chamber stores the pump, microprocessor and electric components if any, the valves, the scrubbing system, the sterile air filters and, optionally, additional components. The scrubbing system is connected to the exhaust port and includes tubing having a male end of the EFC 12 Series Quick Disconnect Couplings. Distal to the exhaust port, the tubing is connected to a pump (Gast, Benton Harbor, Mich.; Model DOA-P104-AA; 35 lit/minutes flow rate), followed by columns that comprise the scrubbing system. One column is filled with Purafil Select (Doraville, Ga.); the other is filled with Purakol (approximately 200 to 300 grams of material for each column). NO is injected into the upper sterilization chamber and held for a 5 minute period. After 5 minutes, the scrubbing system is engaged by attaching the male end of the EFC 12 Series Quick Disconnect Couplings to the female end of the exhaust port, thus opening the port, and activating the pump. Prior to pump activation, the pump exhaust is reconnected to the sterilization chamber via the same port that is used to add NO to the sterilization chamber, using tubing ending with a male end of the EFC 12 Series Quick Disconnect Couplings, and also comprised of a sterile air filter (ACRO 50, Pall Corporation, Port Washington, N.Y.). The gas from the sterilization chamber is sampled using a syringe from an in-line sampling vessel fitted with a rubber septum after 1 minute of pumping. The sampled gas is then injected into and quantified by the ThermoEnvironmental (Waltham, Mass.) 42C chemilluminescent $NO_x$ detector. In addition, NO from the NO storage vessel is injected on the machine as a positive control. The system can recirculate, for example, by adding the gas, disconnecting the gas generation chamber, add tubing from the exhaust port, back to the "intake" port where the NO was added originally, and, when the pump is turned on, the gas recycles through the system.

One set of experiments is performed in quadruplicate on the device using 1% added NO. After one minute of recirculating the gas from the exhaust port back through the intake port (using sterile air filters to eliminate contaminating the sterilization chamber), as described above, sampling the gas content of the sterilization chamber and measuring showed that virtually all of the NO and $NO_x$ components are removed. Each of the four samples barely raised the baseline of the NO detector, resulting in a reading estimated to be approximately 2 ppb, far below the OSHA guidelines of 25 ppm for NO and 1 ppm for $NO_2$.

Experiments are performed using 5% added NO. One liter of air (5%) is removed from the sealed case prior to addition of 5% NO, so that the experiment is performed at atmospheric pressure. One liter of NO is then added to the sealed sterilization chamber and allowed to remain for 5 minutes. The scrubbing system is then activated as described above. After one minute of gas recirculation, samples showed approximately 4 ppb for NO and $NO_x$, in each experiment, again far below OSHA guidelines. The Purafil Select and Purakol columns are not changed over the course of these 6 experiments.

Example 5

A glass pressure vessel is connected to a scrubbed NO gas tank source. The pressure vessel is purged five times with Argon gas to eliminate atmospheric oxygen (preventing formation of $NO_2$.) and an additional three purges of NO are used to ensure a pure NO atmosphere and consistent results of bactericidal activity. To test the sterilization method, *Bacillus subtillis* var *niger* 9372 is used (after obtaining >80% endospore formation; a standard for ethylene oxide and autoclave test sterilization), as well as organisms commonly found on the epidermis: *Staphylococcus aureus* (strain 21769) and *Staphylococcus epidermides* (strain 21977), and the enteric organisms: *Klebsiella pneumoniae* (strain 21991) and *Serratia marcesens* (strain 21140). This particular *Serratia* strain has been found in previous studies to be one of the most resistant bacteria to the bactericidal effects of NO in culture. See, Raulli R et al., Recent Res Devel Microbiol 6: 177-183, 2002, the entire contents of which is incorporated by reference herein.

The organisms are cultured overnight in brain heart infusion BHI. The cultures contain at least $10^8$ CFU/ml based on standardized $ABS_{595}$ curves for each organism. Stainless steel strips, 3×1 cm, are dipped in the cultures, and either dried in ambient air first or placed in the pressure vessel still wet from the culture dip. The strips are exposed to NO gas at atmospheric pressure for decreasing time periods starting with 45 minutes and working back to 5 minutes. Control samples are handled identically, except the pressure vessel is gassed with nitrogen.

TABLE 2

Results from Pressure Vessel Experiments at Five Minute Sterilization Cycle

|  | Bacillus subtilis | Serratia marcesens | Staphylococcus epidermides | Klebsiella pneumoniae | Staphylococcus aureus |
|---|---|---|---|---|---|
| Stainless steel | 3/3 Killed | 3/3 Killed | 3/3 Killed | 3/3 Killed | 3/3 Killed |

The sealed vessel is carefully opened in a laminar flow hood after all the NO had been purged with Argon. The samples are removed aseptically with sterilized tongs and placed in culture tubes containing sterile BHI media. The samples are incubated in a vigorously shaking waterbath at 35° C. The samples are observed (digitally photographed) 24 hrs later, placed back in the waterbath and are measured for absorbance 72 hrs later. The controls had >$10^8$ CFU/ml after 24 hrs. The results shown in Table 2 are from three separate experiments and the results (3/3) indicate that 3 out of 3 trials showed no bacterial growth.

Example 6

Similar to Example 1, a portable system is devised using blood storage containers and other laboratory items. In this construct, a blood storage container (Nexell, Irvine, Calif.; Lifecell PL732 plastic tissue culture flask) serves as the sterilization chamber. It has multiple ports, is easily attached to tubing or other chambers, and is easily cut and heat sealed for insertion and removal of contaminated/sterilized samples. The heat seal is strong and holds well at pressure, even though 1 ATM of pressure is used experimentally. Two 60 ml syringes connected to each other and a line of tubing by a three-way stopcock are employed to mix acidic buffer in one syringe with NO-releasing diazeniumdiolate in the other syringe. The tubing is connected to the blood container/sterilization chamber.

The stopcock is turned so that the acidic buffer can be added to the syringe containing the diazeniumdiolate. The valve is immediately closed to the buffer syringe and opened to the sterilization chamber. The 300 cc sterilization chamber inflates in about 15 seconds. Experiments are performed as described above, except that the devised system is used instead of the pressure vessel.

The test organisms are cultured overnight in BHI. The cultures contained at least $10^8$ CFU/ml (100-fold greater than FDA testing guidelines) based on standardized $ABS_{595}$ curves for each organism. Stainless steel strips, 3×1 cm, are dipped in the cultures, and either dried in ambient air first or placed in the pressure vessel still wet from the culture dip. The dried samples are dipped in sterile BHI media before being placed in the sterilization chamber. This prototype is shown to exhibit bactericidal activity against wet dipped stainless steel strips contaminated with *B. subtilis* (endosporulated), *B. subtilis* (vegetative), *S. marcesens*, or *S. epidermides* in 15 minutes and it may be possible to achieve sterilization in less time.

TABLE 3

Results from Fifteen Minute Sterilization Cycle

|  | Bacillus subtilis (spore) | Bacillus subtilis | Staphylococcus epidermides | Serratia marcesens |
|---|---|---|---|---|
| Stainless steel strip | 2/2 Killed | 2/2 Killed | 3/3 Killed | 3/3 Killed |

Example 7

In this Example, the sterilization of medically relevant materials, such as needles and plastic tubing, is tested. Teflon (⅛' ID), polyethylene (1.77 mm ID), vinyl (0.5 mm ID) tubing and a 30 gauge disposable needle are dipped in a bacterial cocktail containing *B. subtilis*, *S. marcesens*, and *S. epidermides* at about $10^8$ total CFU/ml The samples are placed in the sterilization chamber and sealed. In each case, the lumen (the inner open space or cavity within the tubing) of the tubing or the needle contained at least some visually confirmed inoculum. Table 4 shows the results from the study. The controls for each material reached at least $10^6$ total CFU/ml in 24 hrs as determined by $ABS_{595}$ standardization curves.

TABLE 4

Sterilization of Medical Materials

|  | Vinyl Tubing 0.5 mm ID | Polyethylene Tubing 1.77 mm ID | Teflon Tubing 1/8' ID | Disposable Needle 30 gauge. |
|---|---|---|---|---|
| 15 min Sterilization Cycle | 2/2 Killed | 2/2 Killed | 2/2 Killed | 2/2 Killed |

Example 8

Humidity Effects on Live Bacteria

This Example tests several humidifying paradigms and the ability to sterilize through a gas sterilization seal pouch. A cocktail of bacteria is used, grown to about $10^8$ CFU/ml and mixed in equal volume. Stainless steel strips are dipped, allowed to dry, and subject to one of three methods: A, B and C. Method A samples are wrapped in a moist Kimwipe. Method B samples are left dry. Method C samples are dried and sealed in a V. Mueller™ Dual Peel Seal Pouch, which is designed for gas and autoclave sterilizations. Samples from methods B and C are placed in the sterilization chamber with a moist Kimwipe. Placement in the chamber is done so as to insure maximal separation of the Kimwipe and the sample(s). The chamber is re-sealed carefully so as not to disturb the positioning of the samples relative to the Kimwipe. Each sample is exposed to a 15 minute sterilization cycle at 1 atmosphere, removed under sterile conditions, and the samples are placed in BHI media as described above. Experimental samples are exposed to NO gas while control samples are handled identically, except that the chamber is gassed with nitrogen. The results are shown in Table 5. All controls reached greater than $10^6$ total CFU/ml in 24 hrs as determined by $ABS_{595}$ standardization curves.

TABLE 5

Effect of Moisture on Sealed and Unsealed Dry Samples

| Sample | Method A Moist Kimwipe | Method B Dry | Method C Dry, Sealed |
|---|---|---|---|
| 15 min Sterilization cycle | Killed 2/2 | Killed 2/2 | Killed 2/2 |

This experiment suggests two highly significant findings. One is that sterilization of samples contaminated with live bacteria do not require added moisture from a Kimwipe, since NO sterilized dry samples within the chamber. The second is that the sterilization can occur within a sealed wrapper, which can preserve the sterility of the instrument after the chamber is opened. When this sterilization method employs a gas generating compound, it provides a lightweight method that requires no electrical power and is highly transportable.

Example 9

Humidity Effects on Spores

This Example illustrates the effects of humidity on the sterilization of spores using both NO and $NO_2/N_2O_4$ as sterilizing gases. Tests are conducted in 300 ml glass vessels. The test procedure is as follows: Half of the vessels are humidified by adding 40 micromilliliters of water in the vessel and sealing the vessel with Parafilm. On the inside of the vessels that are prehumidified with 40 ml of water, water condensate is visible over the course of the tests, indicating a high level of humidity in such vessels. The vessels into which no water was introduced showed no condensate on the inside wall of the vessel.

The vessels are allowed to stand for 30 minutes. Two Tyvek sachets, each containing a Biological Indicator manufactured by Raven (product number 3367771 3-6100ST) are placed in each vessel. The vessels are purged as follows: The vessel is evacuated to 8" Hg absolute. The Vessel is re-filled with air to atmospheric pressure. Evacuation/filling is repeated two more times. The vessel is evacuated to 8" Hg absolute. Sterilizing gases are introduced into the vessel. Compressed air (9% Relative Humidity) is added until the vessel reaches atmospheric pressure. The sachets are allowed to remain in the sterilizing environments for either five or ten 10 minutes before being removed and the BI is cultured in 4 milliliters of Tryptic Soy Broth for 14 days at 55-60° C.

Results are shown in the following Table 6.

TABLE 6

| Test Number | Oxide of Nitrogen Used | Diluent | Nitrogen Oxide Concentration (%) | Sterilization Exposure Time (Minutes) | Humid or Dry Condition | Spore Condition in 14 Days |
|---|---|---|---|---|---|---|
| 1 | $NO_2/N_2O_4$ | Air | 5 | 5 | Humid | Dead |
| 1A | $NO_2/N_2O_4$ | Air | 5 | 10 | Humid | Dead |
| 2 | $NO_2/N_2O_4$ | Air | 5 | 5 | Dry | Alive |
| 2A | $NO_2/N_2O_4$ | Air | 5 | 10 | Dry | Alive |
| 3 | NO | Air | 5 | 5 | Humid | Dead |
| 3A | NO | Air | 5 | 10 | Humid | Dead |
| 4 | NO | Air | 5 | 5 | Dry | Alive |
| 4A | NO | Air | 5 | 10 | Dry | Alive |
| 5 | $NO_2/N_2O_4$ | Nitrogen | 5 | 5 | Humid | Dead |
| 5A | $NO_2/N_2O_4$ | Nitrogen | 5 | 10 | Humid | Dead |
| 6 | $NO_2/N_2O_4$ | Nitrogen | 5 | 5 | Dry | Alive |
| 6A | $NO_2/N_2O_4$ | Nitrogen | 5 | 10 | Dry | Alive |

These tests illustrate the importance of humidity in killing spores. In additional sterilization cycle tests, spores are also killed at room temperature in humidity levels between 40% and 80% Relative Humidity.

Example 10

Testing of Powdered Acids

A preferred sterilant gas-generating composition is comprised of a nitrogen-based diazeniumdiolate and oxalic acid. Addition of the oxalic acid in a 10:1 molar ratio with the diazeniumdiolate provides produces the sterilant gas, NO, from the diazeniumdiolate, filling a blood storage container in about 20 sec. This capability eliminates the necessity to add 3N HCl to the diazeniumdiolate to generate NO, instead allowing the addition of water to activate the release of NO gas. The elimination of the need for acid makes the device significantly more convenient to ship, store, and use.

A disposable, plastic gas generation chamber that can be pre-filled with a carbon-based diazeniumdiolate (nitrogen-based diazeniumdiolates can possibly decompose to form carcinogenic nitrosamines) plus an activating powdered acid, have a large, capped opening to ease the addition of water, and have appropriate attachment lines to transport the gas into the sterilization chamber. Other utility lines or ports may be subsequently added to pull a vacuum if necessary, and to release NO gas from the chamber (through a reusable $NO_x$ scrubbing system).

A polyolefin material chosen for its flexibility, puncture resistance, lightweight, and ease of manufacture. The size is approximately a flat 10 inch square. The sterilization chamber's bottom edge has a tabbed "Ziploc" like re-sealable opening, allowing quick and easy loading of instruments and re-sealing. After the user places the instruments in the pouch, the top portion of the pouch is sealed with a simple quick motion of the tab, resulting in a complete gas tight seal.

One edge of the pouch sterilization chamber has an embedded tubing port and approximately 10 inches of tubing to provide a connection to the gas generation chamber. The end of the delivery tube are "quick disconnect" fittings to facilitate easy connection to the gas generation chamber, and each piece of tubing has compressing roller valves to seal the tube.

The chamber is made of a polyolefin material, be 3.5 inches square, and has a large hard plastic screw cap protruding from the top side of the container for easy filling of powders and water. The chamber has a lure lock port to allow easy connection to the sterilization chamber.

Example 11

NO Gas Generation from Nitrite Metal Salts

Nitric oxide is generated using solid nitrite metal salts (for example, sodium nitrite, potassium nitrite, magnesium nitrite) and reacting with either a liquid acid solution (for example, sulfuric acid, maleic acid, hydrochloric acid, nitrous acid, nitric acid) or proton donors in solution to form nitric oxide and/or nitrogen dioxide. Nitric oxide may also be generated by preparing solutions of nitrite metal salts and reacting the solution with solid acid powders to form nitric oxide and/or nitrogen dioxide. If the metal salt and the solid acid powders are mixed in powder forms, the addition of water will initiate the reaction of the two powders. Nitric oxide gas is generated utilizing both nitrite metal solutions and acid solutions. Nitrous acid can be formed during these types of reactions; the nitrous acid can decompose over time to form nitric oxide and nitrogen dioxide. The NO gas can be used to sterilize Biological Indicators or objects and materials, using the method and system of the present invention.

For example, maleic acid and NaNO2 are added to a 20 mL vial; the vial is placed in 1 L jar. Two BI's (Raven Lot# 3367552) in closed sachets (tyvek facing toward NO generating system) are placed inside the 1 L jar. 5 mL of water is added to the powder using a syringe. After 10 minutes, the BI's are placed in 4 mL tryptic soy broth for 14 days at 55-60° C. Alternatively, the BI's in sachets can be taped to the side of the 1 L jar taped so that the tyvek faces the NO source. Also, air may be removed from jar. A vial containing maleic acid and NaNO2 within the jar can be injected with water using a needle. After 10 minutes, the BI's are placed in 4 mL tryptic soy broth for 14 days at 55-60° C. Alternatively, a water soluble capsule can be used to hold a mixture of powdered maleic acid and powdered NaNO2, which is then dissolved with water at the start of the sterilization cycle.

Table 7 illustrates a variety of combinations of sodium nitrite and maleic acid quantities and ratios that can generate adequate quantities of NO gas to sterilize a Biological Indicator in the time indicated.

TABLE 7

| Maleic Acid Quantity (g) | Amount NaNO$_2$ | Exposure time (min) |
| --- | --- | --- |
| 1.01 | 0.503 | 10 |
| 1.028 | 0.509 | 10 |
| 1.001 | 0.5 | 10 |
| 1 | 0.504 | 10 |
| 1 | 0.518 | 10 |
| 1.01 | 0.504 | 10 |
| 1 | 0.506 | 10 |
| 1.03 | 0.374 | 10 |
| 1.01 | 0.33 | 10 |
| 1.16 | 0.332 | 10 |
| 1.01 | 0.255 | 10 |
| 1 | 0.109 | 60 |
| 0.2538 | 0.1258 | 30 |
| 0.257 | 0.128 | 30 |
| 0.25 | 0.131 | 30 |
| 0.25 | 0.125 | 30 |
| 0.25 | 0.119 | 30 |
| 0.255 | 0.128 | 30 |
| 0.223 | 0.127 | 20 |
| 0.2477 | 0.1312 | 20 |
| 0.244 | 0.132 | 10 |
| 0.2478 | 0.1326 | 10 |
| 0.246 | 0.119 | 5 |

Example 12

Synthesis of a Soluble, Carbon-Based Diazeniumdiolate

While a variety of nitrogen-based diazeniumdiolates are commercially available and would work in this application, the ability of nitrogen-based diazeniumdiolates to form highly carcinogenic nitrosamines limits their use in medical applications (Parzuchowski et al., 2002, cited above). The carbon-based diazeniumdiolates cannot form nitrosamines and can produce up to three times more NO on a molar basis than nitrogen-based NO donors. By using a carbon-based NO donor, the margin of safety for the product is increased while decreasing the total weight.

A carbon-based diazeniumdiolates can be produced through the use of a benzylic intermediate. Benzyl methyl ether, $PhCH_2OCH_3$ (commercially available from Sigma-Aldrich, St. Louis, Mo.) is one starting material. In a Parr pressure vessel, 3 ml (0.024 moles) of benzyl methyl ether is added to 30 ml of methanol. To this solution, 11 ml (0.048 moles) of 25% sodium methoxide is added with stirring. Oxygen is removed from the flask by alternating cycles (10) of inert gas pressurization and venting. The solution is then exposed to between 40 and 80 psi NO gas at room temperature for 1 to 5 days. When no more NO gas is being consumed, the reaction is complete, and the head space is purged of NO gas. Diethyl ether is then added to precipitate out all of the anionic diazeniumdiolated salts, which may then be filtered and dried. The product, $PhC(N_2O_2Na)_2OCH_3$ is tested for its ability to release NO using a chemilluminescent method described below as well as subject to structure verification by spectrophotometry, elemental analysis, and NMR confirmation.

An alternate synthetic scheme can be derived from the commercially available benzyl thiocyanate ($PhCH_2SCN$, Sigma-Aldrich, St. Louis, Mo.). In a Parr pressure vessel, 3 g (0.020 moles) of benzyl thiocyanate is added to 30 ml of tetrahydrofuran. To this solution, 40 ml (0.040 moles) of 1.0 M sodium silanolate is added with stirring. Oxygen is removed from the flask by alternating cycles (10) of inert gas pressurization and venting. The solution is then exposed to between 40 and 80 psi NO gas at room temperature for 1 to 5 days. When no more NO gas is being consumed, the reaction is complete, and the head space is purged of NO gas. Diethyl ether is then be added to precipitate out all of the anionic diazeniumdiolated salts, which may then be filtered and dried. The product, $PhC(N_2O_2Na)_2SCN$ is tested for it ability to release NO using a chemilluminescent method described below as well as subject to structure verification by spectrophotometry, elemental analysis, and NMR confirmation.

Preferred sterilant gas-generating compounds are these carbon-based diazeniumdiolate compounds for generating NO because their NO release rate under acidic conditions rapid and close to identical. The likely criteria for choice of NO donor is yield and cost.

Example 13

Determination of NO Release from Diazeniumdiolates

The method for determining the NO released from diazeniumdiolates is conducted according to the method of Smith D J et al., J Med Chem 39:1148-1156, 1996, the entire contents of which is incorporated herein. Weights of the samples is recorded and placed in 0.1 M phosphate buffer (pH 7.4) and the mixture is allowed to stand open to the air at 25° C. in a water bath. The buffer is then purged with argon gas via a fritted glass tube at the bottom of the vessel, such that the gaseous effluent gas is passed through a chemilluminescent $NO_x$ detector calibrated to measure NO content. Bubbling is continued until a steady and horizontal trace is achieved, whereupon the signal is integrated over a span of several minutes. The number of integral units are converted to a value for moles of NO by comparisons with integrals obtained for certified gaseous standards of NO in helium (MG Industries, Morrisville, Pa.). The rate of NO release over that time increment, calculated by dividing the integrated signal by the number of minutes the integration is conducted, are plotted versus the total elapsed time since the sample was first placed in the buffer.

Example 14

Environmental Containment of NO

All experiments involving NO are performed in a certified fume hood. NO is an environmental pollutant and may be harmful to humans at concentrations higher than 100 ppm. NO contained in synthesis vessels or in sterilization chambers are bled into a container that holds 10-fold the volume of ambient air for a duration of 5 minutes. This step serves to turn all of the NO into $NO_2$. The $NO_2$ from the chamber then passes over a column of NaOH, which effectively scrubs out the $NO_2$. This is a well characterized method commonly used in industrial processing (Basile, 2002).

Example 15

Optimization of Sterilization Cycle at Ambient Temperature

The following parameters are optimized for a sterilization cycle at ambient temperature (~22-24° C.), the cycle duration percent air allowable, humidity, internal pressure (amount of NO), and instrument characteristics (surface area of instruments, types of instruments [i.e., narrow lumens, dead end lumens], use of pre-packaged materials in sterilization pouches, salt-crusted instruments, protein crusted instruments). The biological indicator (BI) organism chosen for testing is sporulated *Bacillus subtillis* var *niger*, which is the standard organism used for $Et_2O$ process validation and is also commonly used for other sterilization process validation. See Hoxey E V et al., J Appl Bacteriol 58: 207-214, 1985, which is incorporated herein by reference in its entirety.

*B. subtillis* var *niger* 9372 is cultured overnight in Luria Broth (LB) media at 37° C. in a shaking waterbath. This usually results in a culture of greater than $10^8$ CFU/ml. The $ABS_{595}$ is measured for each overnight culture and compared to a standard curve to determine the approximate CFU/ml. The density of the cultures is adjusted to $10^6$ CFU/ml by dilution with sterile LB. The *bacillus* is sporulated according to the following method. The cultures are centrifuged at 2500 RPM (1000×g, Sorvall GLC-1) for 5 minutes and resuspended in a low nutrient salt media as described by Sterlini and Mendelstam, Biochem J. 113:29-37, 1969 (1969). The bacteria are washed twice more in this sporulation media, and the final pellet suspended in an appropriate amount of sporulation media to retain a density of $10^6$ CFU/ml. This method typically results in greater than 80% endospore formation.

Paired stainless steel strips, Teflon® tubing sections 1" long, ⅛" inner diameter (I.D.), and (polyethylene)terephthalate (PET) strips are used for general studies of the Sterilization Cycle. Parameters studies. These three materials, stainless steel strips, Teflon tubing and PET strips are referred to as the "Materials Panel" Items from the Materials Panel are dipped in $10^6$ CFU/ml of the endosporulated bacillus suspension. Paired material samples are handled identically, with the control materials being placed in a sterilization chamber and exposed to nitrogen under the same conditions as the group undergoing sterilization with NO gas. After processing, the materials are placed in LB media for incubation at 37° C. in a shaking waterbath for 24 hrs. The culture broth for control and processed groups are observed visually and photographed at 24 hrs. An aliquot is removed, serially diluted with sterile LB, and plated onto LB agar plates to determine the CFU/ml. The culture is incubated for an additional 24 hrs to total 48 hrs, and if needed the $ABS_{595}$ is measured at 48 hrs (along with additional confirmatory photographs). The inoculated LB agar plates are incubated for 37° C. and assessed for colony growth 24 and 48 hrs after plating.

Any plate colonies that arises from materials that have been through the sterilization process is tested to confirm the identity of the bacteria as *B. subtillis* var *niger* through morphological, Gram stain and/or other necessary means. The same confirmatory step applies to any cultures in LB that turn positive. Any tested parameter that results in material(s) that exhibit a *B. subtilis* var *niger* positive culture after being exposed to the sterilization process is considered a parameter beyond the usable range.

Example 16

Assessment of Sterilization Cycle Duration on Sterilization Efficacy

Sterilization of the materials are tested at 5, 10, 20, 40, 80, and 120 minutes at room temperature on the Materials Panel. For each processed group, a control group is treated identically, with the exception of using nitrogen gas instead of NO. The experiments are repeated three times, and the criteria for successful sterilization at any particular time point is 0 CFU/ml in all three trials. One failure (positive *B. subtillis* var *niger* culture) in three trials is considered a failure at that measurement.

Example 17

Effect of Ambient Temperature on Sterilization Efficacy

Items from the Materials Panel are dipped in $10^6$ CFU/ml *B. subtillis* in LB. An appropriate time point is selected using data from the previous experiment, using the penultimate minimal successful time point. For example, if 5 minutes is successful, then 10 minutes is used. Experiments are performed from −10° C. to 50° C. in ten degree increments. Should either of the extreme temperatures fail to produce a successful outcome, the temperature is increased or decreased by 10° C. and the trial repeated until a successful outcome is reached. Cold experiments are performed in a calibrated refrigeration unit capable of temperatures from −20° to 20° C. Beyond 20° C., the experiments are performed in a standard incubator. The sterilization device components are equilibrated to the test temperature for 20 minutes prior to the sterilization process trial. For each processed group, there is a control group treated identically, with the exception of using nitrogen gas instead of NO. A successful outcome at any temperature point is 0 CFU/ml in all three trials. One failure (positive *B. subtillis* var *niger* culture) in three trials is considered a failure at that measurement therefore setting the limit at the measured parameter.

One possible interdependency would be the relationship between higher ambient temperatures and NO gas pressure used in the process. It may be reasonably predicted that higher temperatures may result in an equal or greater degree of efficacy with less NO gas pressure. This would not necessarily be a problem. A problem that may surface is the ability to humidify the sterilization chamber under freezing temperature conditions. In this case, the inability to humidify the chamber may impose a limit on utilization of the process in freezing temperatures.

Example 18

Evaluation of Optimal Humidity Conditions in the Sterilization Chamber

A manufactured sterilization chamber prototype is altered to allow the insertion of a hygrometer probe. The probe is sealed inside the chamber using a non-hardening silicon sealant. A NIST traceable hygrometer (Fisher Scientific) with a range of 2 to 98% relative humidity (RH) is used to measure humidity levels. The calibration of the meter is checked once a week using dedicated nitrogen-gassed chambers containing salt baths mixed to generate RH environments of between 10 to 80%, such as 11, 43, and 75%.

The method producing reproducible RH levels in the sterilization chamber is established, and thereafter, items from the Material Panel are contaminated with *B. subtillis*, allowed to dry in ambient air, placed in the sterilization chamber along with an appropriate weight of water (absorbed on swatches) and the sterilization process is tested along the linear range of RH achievable in increments from 10-80% RH, for example 10 to 15% RH, 20%, 30%, 40%, 50%, 60%, 70% and 80% RH. Experiments performed at test temperatures other than room temperature first equilibrate at the test temperature for 20 minutes prior to beginning the sterilization process. Again, the penultimate minimal effective time point is used. A successful outcome at any RH level is 0 CFU/ml in all three trials. One failure (positive *B. subtillis* var *niger* culture) in three trials is considered a failure at that measurement therefore setting the limit at the measured parameter.

For example, if the sterilization fails at 0% RH but is effective at 15%, then additional experiments are conducted to identify the precise % RH between 0 and 15% to optimize the range of effective conditions for the humidification and/or desiccation needed in the sterilization chamber.

Example 19

Effect of NO Gas Pressure on Sterilization Efficacy

A low pressure gauge is fitted to the sterilization chamber tubing. A three-way stopcock (lure lock) is adapted to the gauge directly or via a short length of tubing. From there a vacuum can be pulled with a 60 cc syringe or pump if required. The chamber can be sealed with the stopcock, thus maintaining the vacuum. The NO gas pressure used for the sterilization trial is regulated by altering the mass of diazeniumdiolate in the gas generation chamber from the normal level of 6.8 gm per 1000 cc of volume. Sterilizations are attempted using 1.7, 3.4, 6.8 gms (control) of diazeniumdiolate in the gas generation chamber, keeping the 10:1 ratio of oxalic acid throughout the experiment. Dead space is also accounted for. A successful outcome is 0 CFU/ml in three trials. One failure (positive *B. subtillis* var *niger* culture) in three trials is considered a failure at that measurement, therefore setting the limit at the measured parameter.

Example 20

The Effect of Ambient Air on Sterilization Efficacy

The inclusion or exclusion of ambient air is a critical parameter, as the ultimate mechanism of NO sterilization in this method can include the formation of nitrous acid ($HNO_2$) on surface condensates. A small percentage of ambient air may be advantageously included in the process. The small amount of $O_2$ dissolved in a humid condensate can also suffice to produce enough nitrous acid under conditions used in the method of the present invention.

A low pressure gauge is fitted to the sterilization chamber tubing. A three-way stopcock (lure lock) is adapted to the gauge directly or via a short length of tubing. From there a vacuum can be pulled with a 60 cc syringe or pump if required. The chamber can be sealed with the stopcock, thus maintaining the vacuum. Graduated syringes filled with ambient air can be attached to the stopcock and a known quantity of air can be added to the sterilization chamber. The amount of diazeniumdiolate in the gas generation chamber is adjusted based on 2 mol of NO per mol of diazeniumdiolate and using the Ideal Gas Law to reach what would be 1 ATM in 1 L, or 6.8 gm per liter of volume. Dead space is determined and be accounted for with diazeniumdiolate mass. Volumes of ambient air representing 1, 2.5, 5, 10, 15, and 20% in the sterilization chamber is tested. These trials are performed at 25° C., and 2 relevant extremes of temperature determined from experiments outlined above. Zero growth from *B. subtilis* contaminated items from the Material Panel in three trials is considered a successful outcome. One failure (positive *B. subtillis* var *niger* culture) in three trials is considered a failure at that measurement therefore setting the limit at the measured parameter. A failure at the low level(s) of ambient air may be an indication that oxygen is required, thus providing further evidence that the mechanism of action for NO in this process may be related to the formation of nitrous acid.

The potential for an interdependency between ambient air and humidity has been previously discussed.

Example 21

Sterilization using a Variety of Oxides of Nitrogen

A mixture of nitric oxide and air will react, resulting in a mixture containing many different oxides of nitrogen. The concentration of each nitrogen-oxide species that is present in a mixture will vary with temperature, pressure, and initial concentration of the nitric oxide. The concentrations of various nitrogen-oxide species in air can be measured directly or predicted using established methods.

For example, the detailed chemical kinetics of NO oxidation in humid air can be simulated using available chemical kinetics software (such as CHEMKIN software) and kinetics data found in the literature. In one approach to predict the composition and concentrations of species that result from a NO-air mixture, a closed homogeneous batch-reactor model is used.

The results of the analysis for two different initial concentrations of NO are shown in Table 6 below. These results show that after five minutes, the NO is oxidized to NO2, N2O4, nitric acid, nitrous acid HNO3, and smaller amounts of N2O3 and N2O5.

Table 8 Predicted Concentrations of Oxides of Nitrogen at Room Temperature (75° F.) and 70% Relative Humidity

TABLE 8

| | | |
|---|---|---|
| Initial Mole Fraction NO in Air | 3.00E−02 | 10.00E−02 |
| Mole Fraction NO (5 minutes) | 7.51E−04 | 1.11E−03 |
| Mole Fraction NO2 (5 minutes) | 2.24E−02 | 5.87E−02 |
| Mole Fraction N2O4 (5 minutes) | 3.68E−03 | 2.39E−02 |
| Mole Fraction HONO2 (5 minutes) | 3.50E−05 | 1.18E−04 |
| Mole Fraction HNO2 (5 minutes) | 2.91E−08 | 5.49E−08 |
| Mole Fraction N2O3 (5 minutes) | 3.87E−06 | 1.41E−05 |
| Mole Fraction N2O5 (5 minutes) | 2.01E−11 | 2.16E−10 |
| Mole Fraction H2O (5 minutes) | 2.01E−02 | 1.96E−02 |

Another embodiment of the system and method of the present invention uses a sterilant gas comprised of nitrogen dioxide and/or other oxides of nitrogen such as di-nitrogen tetroxide. These oxides of nitrogen can be generated from nitric oxide and air supplied by the gas generating chamber. In another embodiment, nitrogen dioxide and/or di-nitrogen tetroxide can be delivered from a pressurized tank. $NO_2$ or $N_2O_4$ can be stored in high concentrations in a tank or can be diluted to lower concentrations in a mixture with either an inert gas, such as nitrogen or argon. Alternatively, the $NO_2$ or $N_2O_4$ could be diluted with air.

The gas or gas mixture can be delivered to the sterilization chamber through a metering regulator in fluid connectivity with the sterilization chamber or other gas delivery method known to one skilled in the art.

Example 22

Sterilization Effectiveness Using a Variety of Oxides of Nitrogen

The experiments are conducted in glass vessels in which gases can be metered in exact amounts. The tests were conducted using biological indicators made of stainless steel disks inoculated with $10^6$ bacillus stearothemophilus spores. The BI disks are heat-sealed in individual TYVEK sterilization pouches and placed in a glass vessel. The vessel is filled with various mixtures of gases following specific protocols for the order and timing of gas introduction.

In one protocol, the glass vessel is evacuated to 3" Hg absolute. Either NO or $NO_2$, as the sterilant gas, is added in an amount that corresponds to a 5% concentration (by volume) when the vessel is completely filled with sterilant gas and diluent gas. After 5 minutes, either air or nitrogen was added to the vessel until atmospheric pressure is reached. The BI is exposed to the air or nitrogen for 10 minutes. Thereafter, the BIs, in their pouches, are removed from the vessel and taken to a microbiological hood. The biological indicators are removed from the pouches and placed in tubes with sterile tryptic soy broth, incubated at from about 55 to about 60° C., and monitored for growth.

The results of a spore study is shown in Table 9.

TABLE 9

Results of Spore Studies in NO and $NO_2$

| Exp Time | 5% $NO_2$ in Air with Humidity Chip | 5% NO in Air with Humidity Chip | 5% $NO_2$ in $N_2$ with Humidity Chip |
|---|---|---|---|
| 10 min | Dead | Dead | Dead |
| Control | Live | Live | Live |

Example 23

Sterilization Cycles Including Exposure Periods with Particular Oxides of Nitrogen The ability of the nitrogen oxide gases to penetrate an inner open space or cavity within a tube (i.e., a lumen) and inactivate spores in the lumen is evaluated. The spores used are those that are most resistant to the nitrogen oxide gases.

The following configuration of lumens are tested:

(a) 17" stainless (SS) tubes having a 2.5 mm inner diameter (I.D.), bent in "U" shape (b) 60" polyethylene (PE) tube having a 4.5 mm ID, coiled and in Tyvek pouch (c) 60" PE tube having a 4.5 mm ID and a 1.5 mm outer diameter (O.D.) PEEK tube inside, coiled and in Tyvek pouch Wire biological indicators are inoculated with $10^6$ Bacillus stearotheinophilus spores (ATCC 7953), (Raven Lot 3W67583) and placed at the center point of the tube in each of these configurations. The coiled polyethylene tubes were then heat-sealed in a TYVEK sterilization pouch.

Separately, each of the lumen samples are tested. The stainless steel tube (triplicate samples: SS-1, SS-2, and SS-3), the polyethylene tube, and the polyethylene tube with the PEEK catheter were each placed in a resistometer and exposed to the following gas cycle for 5 minutes at 23° C. This gas cycle is defined as follows:

The sterilization chamber/resistometer is evacuated and held at vacuum for 2 minutes. NO gas is then added to the sterilization chamber until the vacuum is decreased by 1" Hg. This condition is maintained for 2 minutes. Are is then added until the chamber reaches atmospheric pressure and the condition is held for 5 minutes.

The results of the spore studies are shown in Table 10. After 14 days of incubation, bacterial growth is seen in all of the control samples and in none of the exposed samples after 5 minutes of exposure to the gas.

TABLE 10

Results of Spore Studies in Lumens

| Exposure Time | (a) SS-1 | (a) SS-2 | (a) SS-3 | (b) PE Sheath | (c) PE Sheath with Catheter |
|---|---|---|---|---|---|
| 5 min | Dead | Dead | Dead | Dead | Dead |
| 5 min | Dead | Dead | Dead | Dead | Dead |
| 5 min | Dead | Dead | Dead | Dead | Dead |
| Control | Live | Live | Live | Live | Live |

Example 24

Effect of Insoluble Crystal Occlusion of Sterilization Efficacy

Numerous studies have demonstrated the difficulty, especially with gaseous sterilizing agents, of killing spores occluded within water insoluble crystals. See, for example, Abbott C F et al., J Pharm Pharmacol 8:709-720, 1956; Doyle J E and Ernst R R, Applied Microbiology 15(4): 726-730, 1967. The method of Doyle and Ernst is used for the production and isolation of spores, occlusion of spores in crystalline calcium carbonate, and recovery of occluded spores for determination of sterilization efficacy.

Ten ml solution of 1.11% $CaCl_2$ is prepared containing $10^6$ spores per ml. To this, ten ml of 1.06% $Na_2CO_3$ is added rapidly and the mixture is shaken vigorously. Crystals of $Ca_2CO_3$ will form immediately, occluding large quantities of spores per crystal. The crystals are washed using distilled water in three 20,000×g centrifugation steps. The crystals are brought back to 10 ml in distilled water and 0.2% methylcellulose for easy handing. Ten μl of the crystal suspension is blotted onto strips of filter paper, dried at room temperature, and further dried at 90° C. for 16 hrs.

After exposure to the sterilization agent, the paper strips are placed in 25 ml of sterile 3.0% $NH_4Cl$ for 3 days at 0° C. to dissolve the crystals. The strip and solution is placed in a blender, followed by sonication for 5 minutes. The samples are diluted and plated on tryptone glucose yeast extract agar for counting. Zero growth in three separate experiments is considered a successful outcome.

Example 25

Sterilization Efficacy in Devices Having Long, Narrow and Dead-End Lumens

Many studies have documented the difficulties in reliably sterilizing long, narrow, and dead-end lumens. See, for example, Alfa M C., Infect Control Ster Technol April: 26-36, 1997; and Rutala W A et al., Infect Control Hosp Epidemiol 19: 798-804, 1998. To test the ability of this sterilization process to effectively sterilize these types of devices, non-porous Teflon tubing (<3 mm I.D.) are cut into 125 cm lengths and a culture of *B. subtillis* var *niger* ($10^6$ CFU/ml) is pushed through the tubing using a 60 ml syringe. The tubing is drained and allowed to air dry. Some tubing is plugged at one end with a tight fitting plug. The gas tightness of the plug is tested by applying a small amount of air pressure using a 60 cc syringe. Alternate methods of sealing one end of the tubing include heat sealing, solvent welding, and clamping. Open or sealed end tubing is coiled with care to not crimp the tubing and placed in the sterilization chamber for processing. After the sterilization process is complete, the tubing is cut into 4 inch sections and placed into sterile culture tubes containing enough LB to completely submerge the tubing sections. Sterilization efficacy is evaluated as described above.

Example 26

Sterilization Efficacy in Instruments with Occluded Joints

Surgical scissors and forceps are contaminated to beyond the swivel joint by dipping in contaminated broth at $10^6$ CFU/ml. The swivel joint is actuated while the instrument is submerged in bacterial broth to allow bacteria to get between the arms of the instrument. The instrument is allowed to air dry, and subject to the sterilization process. Zero growth in three separate trials is considered a successful outcome.

Example 27

Sterilization of Instruments in Individual Sterilization Pouches

Surgical scissors and forceps are contaminated to beyond the swivel joint by dipping in contaminated broth at $10^6$ CFU/ml. The instruments are dried and sealed in a V. Mueller™ Dual Peel Seal Pouch Fisher Scientific) and inserted into the sterilization chamber of the device for processing. After processing, the contaminated forceps are carefully removed from the pouches using sterile technique and under sterile conditions, and placed in a culture flask containing sterile LB media, and sterilization efficacy is assessed as described above. Zero growth in three separate trials is considered a successful outcome. Other items, such as long narrow lumen tubing may also be added to this protocol for study.

Example 28

Two Stage Operating Cycle

The overall sterilization effectiveness is dependant on the ability of the gas to come in contact with the microbes, and the effectiveness with which the sterilizing gases kill the microbes they contact. In one preferred embodiment of the sterilizing method of the present invention, the operating cycle for the sterilizing sterilizer maximizes both the penetration of sterilizing gases into devices, as well as the killing of the microorganisms that are contacted. The penetration of a gas into the small crevices, lumens, gaps, cracks, mated surfaces, and interior surfaces of medical devices is dependant (among other things) on the gas molecule size, diffusivity, "stickiness", and tendency to be absorbed into or adsorbed onto the surface of solid or liquid materials.

It has been found that NO has better transport properties than $NO_2$ because it is a smaller, less "sticky" molecule. In a preferred embodiment of the present invention, the sterilization cycle involves a two stage approach. During the first stage, the NO is allowed to penetrate throughout the surfaces of the object to be sterilized. During the second stage, the NO is oxidized to form $NO_2$ and other oxides of nitrogen. The $NO_2$ and other oxides of nitrogen offer additional, effective modes of microbial kill. This two stage approach minimizes the amount of sterilizing gas volume and the time that is needed to sterilize a device that has hidden surfaces and/or a complex geometry.

One example of this preferred two stage operating cycle is conducted as follows. The device to be sterilized is placed in a chamber capable of generating and maintaining a vacuum as well as receiving sterilizing gases and air. The sterilization chamber is sealed. The sterilization chamber is evacuated to a vacuum level of less than 3" Hg absolute. NO gas is introduced to the evacuated chamber in an amount that corresponds to 1-8% concentration in the final sterilizing gas mixture. The conditions are maintained for a period of time from about 30 seconds to about 5 minutes. Humidified air is added until the chamber reaches atmospheric pressure. The conditions are maintained for a period of time from about 30 seconds to about a few hours, depending on the sterilant concentration. The sterilization chamber is evacuated and purged with air before the sterilized device is removed.

This two stage operating cycle is more effective at sterilizing object having a lumen than both (1) a cycle that introduces NO and air simultaneously and (2) a cycle that introduces $NO_2$ in air or nitrogen.

Example 29

Sterilization of Polymers

To determine if a polymer, the polymer is inoculated with the spore solution, dried and exposed to the oxides of nitrogen. After exposure, the spores are washed off the polymer into a growth medium and incubated to assess growth.

The Effect of Nitric Oxide Sterilization Methods on Bioresorbable Polymers.

This Example evaluates the molecular weight profile of polyester-based bioresorbable polymers before and after sterilization treatment over time. Specifically, the effect of three sterilization techniques are evaluated: ethylene oxide (EtO) treatment, gamma irradiation and the method of the present invention using oxides of nitrogen. The polyester materials include LACTEL® DLPLG (poly-DL-lactide-co-glycolide, 50/50), DLPLA (poly-DL-lactide-COOH), LPLA (poly-L-lactide) and PCL (poly-e-caprolactone) polymers purchased from the DURECT Corporation (Pelham, Ala.). Treated samples are evaluated immediately after treatment (Day 0). Samples are treated using the method of the present invention (or industry standard conditions for EtO (100% EtO for 1 hour, 57° C., >70% RH, followed by 15 hour aeration) and gamma irradiation (26.8 kGy). For each sterilization method, untreated control samples of each polymer are prepared.

For all samples treated with $NO_x$, there is no significant change in the MW profile of the bulk polymer. In a few samples there are some small differences noted at the lower MW region (about 10 min retention time) of the chromatogram. The EtO treated samples change shape relative to the control samples, are difficult to remove from the Tyvek® sterilization pouch, and adhere to the surface of the bag. There is no significant change in the MW profile of the bulk polymer. For all irradiated samples tested there is a detectable change in the MW profile of the bulk polymer.

Three sterilization treatments ($NO_x$, EtO and irradiation) are applied to bulk samples of four polyester bioresorbable polymers: LACTEL® DLPLG (poly-DL-lactide-co-glycolide, 50/50), DLPLA (poly-DL-lactide-COOH), LPLA (poly-L-lactide) and PCL (poly-e-caprolactone). The polymer samples are tested upon receipt (identified as Day 0, time point 1 by GPC Chromatography to analyze their molecular weight. Samples treated with the oxides of nitrogen exhibit no significant difference in their MW profile, as compared to the control samples. Although the EtO treated polymer samples display no significant difference in their MW profile, they become visually deformed relative to the control samples and stick to the sterilization pouch. The gamma irradiated polymer samples display a detectable change in the MW with the average molecular weight shifting to a lower value which suggests fragmentation of the bulk polymer chains. The gamma irradiated change is most pronounced for the PCL samples.

Example 30

Protein Sterilization

Under sterilization conditions known to kill *stearothermophilus* spores, a sample protein is tested to determine if the sterilization conditions affect the protein's biological function. Trypsin is used as the sample protein. The trypsin is in powder form during the sterilization cycle and thereafter reconstituted in solution and tested for its functionality. A biological indicator is included in the same sterilization container as the protein powder.

In describing representative embodiments of the invention, the specification may have presented the method and/or process of the invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the invention should not be limited to the performance of their steps in the order written, and one skilled in the art can readily appreciate that the sequences may be varied and still remain within the spirit and scope of the invention.

The foregoing disclosure of the embodiments of the invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

What is claimed is:

1. A method for sterilizing a packaged medical device in a gas-tight sterilizing chamber, the method comprising:
   placing the packaged medical device sealed within a sterilization packaging into a gas-tight sterilizing chamber that contains air;
   sealing the sterilizing chamber;
   evacuating from the sealed sterilizing chamber at least a portion of the air contained in the sterilizing chamber to reach a selected pressure level within the sterilizing chamber;
   after the sterilizing chamber reaches the selected pressure level, supplying the sterilizing chamber with a selected amount of a $NO_2$-based sterilant gas consisting essentially of $NO_2$;
   after supplying the sterilizing chamber with the selected amount of the $NO_2$-based sterilant gas, providing a humidified gas into the sterilizing chamber to form a humidified $NO_2$-based sterilant gas in the sterilizing chamber;
   after providing the humidified gas into the sterilizing chamber, performing a dwelling operation at about room temperature for a selected period of time during which the humidified $NO_2$-based sterilant gas sterilizes the medical device contained within the sterilization packaging;
   removing at least a portion of the humidified $NO_2$-based sterilant gas from the sterilizing chamber; and
   removing the medical device sealed within the sterilization packaging from the sterilizing chamber.

2. The method of claim 1, wherein the sterilant gas is generated from a sterilant gas-generating composition.

3. The method of claim 2, wherein the gas generating chamber contains the sterilant gas-generating composition.

4. The method of claim 2, wherein the sterilant gas-generating composition is comprised of at least one sterilant gas-generating compound.

5. The method of claim 1, wherein the sterilizing chamber further comprises a port for introducing gases.

6. The method of claim 1, wherein the time period is from about 30 seconds to about 20 minutes.

7. The method of claim 1, wherein the time period is from about 30 seconds to about 12 hours.

8. The method of claim 1, wherein the time period is from about 2 minutes to about 24 hours.

9. The method of claim 1, wherein all gases entering the sterilizing chamber have been filtered.

10. The method of claim 1, wherein the sterilizing chamber is purged after the object is exposed to the sterilant gas.

11. The method of claim 1, wherein the selected pressure level is less than 2" Hg.

12. The method of claim 1, wherein the exposure to the sterilant gas includes humidity from about 40% to about 80%.

13. The method of claim 1, wherein a concentration of oxygen in the sterilizing chamber is from about 0% to about 21%.

14. The method of claim 1, wherein the method is conducted at a temperature from about 18° C. to about 30° C.

15. The method of claim 14, wherein the time period is from about 2 minutes to about 24 hours.

16. The method of claim 1, wherein the medical device is an implant.

17. The method of claim 16, wherein the implant is selected from the group consisting of a cardiovascular stent, a peripheral drug-eluting stent, a polymer coated implant, and mixtures thereof.

18. The method of claim 1, wherein the medical device is a stent.

19. The method of claim 1, wherein the medical device is selected from the group consisting of a cardiac surgery product, an orthopedic surgery product, and a dental surgery product.

20. The method of claim 1, wherein the medical device is an implant selected from the group consisting of a cardiac implant, an orthopedic implant, a dental implant, a gastrointestinal implant, and a vascular implant.

21. The method of claim 1, wherein the medical device comprises at least one material selected from the group consisting of Poly(L-lactide), Poly(DL-Lactide), 50/50 Poly(DL-lactide-co-glycolide), Poly(e-caprolactone) and mixtures thereof.

22. The method of claim 1, wherein the medical device comprises metal, non-metal, polymer or plastic, elastomer, or biologically derived material.

23. The method of claim 1, wherein the medical device comprises a material selected from the group consisting of stainless steel, aluminum, nitinol, cobalt chrome, titanium and combinations thereof.

24. The method of claim 1, wherein the medical device comprises a material selected from the group consisting of glass, silica, and ceramic.

25. The method of claim 1 wherein the medical device comprises a material selected from the group consisting of polyacetal, polyurethane, polyester, polytetrafluoroethylene, polyethylene, polymethylmethacrylate, polyhydroxyethyl methacrylate, polyvinyl alcohol, polypropylene, polymethylpentene, polyetherketone, polyphenylene oxide, polyvinyl chloride, polycarbonate, polysulfone, acrylonitrile-butadiene-styrene, polyetherimide, polyvinylidene fluoride, copolymers thereof and combinations thereof.

26. The method of claim 1, wherein the medical device comprises a material selected from the group consisting of polysiloxane, fluorinated polysiloxane, ethylene-propylene rubber, fluoroelastomer and combinations thereof.

27. The method of claim 1, wherein the medical device comprises a material selected from the group consisting of polylactic acid, polyglycolic acid, polycaprolactone, poly-paradioxanone, polytrimethylene carbonate and their copolymers, collagen, elastin, chitin, coral, hyaluronic acid, bone and combinations thereof.

28. The method of claim 1, wherein the medical device further comprises a bioactive coating.

29. The method of claim 28, wherein the bioactive coating is selected from the group consisting of a biocompatible coating, an infection resistance coating, an antimicrobial coating, a drug release coating, an antithrombogenic coating, a lubricious coating and combinations thereof.

30. The method of claim 28, wherein the bioactive coating is selected from the group consisting of heparin, phosphoryl choline, urokinase, rapamycin and combinations thereof.

31. The method of claim 28, wherein the bioactive coating comprises a hydrophilic or hydrophobic coating.

32. The method of claim 28, wherein the bioactive coating comprises a polymer selected from the group consisting of polyvinyl pyrrolidone, polyethylene glycol, polypropylene glycol, polyethylene glycol-co-propylene glycol, polyethylene glycol acrylate, polyethylene glycol diacrylate, polyethylene glycol methacrylate, polyethylene glycol dimethacrylate, polyethylene oxide, polyvinyl alcohol, polyvinyl alcohol-co-vinylacetate, polyhydroxyethyl methacrylate, and polyhyaluronic acid, and hydrophilically substituted derivatives, monomers, unsaturated pre-polymers, uncrosslinked polymers, copolymers thereof and combinations thereof.

33. The method of claim 28, wherein the bioactive coating comprises a polymer selected from the group consisting of polytetrafluoroethylene, polyethylene, polypropylene, poly(ethylene terephthalate), polyester, polyamides, polyarylates, polycarbonate, polystyrene, polysulfone, polyethers, polyacrylates, polymethacrylates, poly(2-hydroxyethyl methacrylate), polyurethanes, poly(siloxane)s, silicones, poly(vinyl chloride), fluorinated elastomers, synthetic rubbers, poly(phenylene oxide), polyetherketones, acrylonitrile-butadiene-styrene rubbers, polyetherimides, hydrophobically substituted derivatives thereof, their precursor monomers, copolymers thereof and combinations thereof.

34. The method of claim 1, wherein the medical device is comprised of a material selected from the group consisting of a bioabsorbable polymer, a drug-bearing polymer and mixtures thereof.

35. The method of claim 1, wherein the medical device is selected from the group consisting of an orthopedic bone graft and a bone scaffold.

36. The method of claim 1, wherein the medical device is a biological product, wherein the biological product is selected from the group consisting of a tissue, an organ, a wound healing product, and a tissue engineering product.

37. The method of claim 1, wherein the medical device is a protein.

38. The method of claim 1, further comprising, after the exposing, scrubbing the sterilant gas.

39. The method of claim 38, wherein the scrubbing comprises passing the sterilant gas through a scrubbing medium to reduce a concentration of $NO_2$.

40. The method of claim 39, wherein the concentration of $NO_2$ is reduced below 1 ppm.

* * * * *